(12) United States Patent
Iwasawa et al.

(10) Patent No.: US 11,885,856 B2
(45) Date of Patent: Jan. 30, 2024

(54) HEAD COIL DEVICE AND MAGNETIC RESONANCE IMAGING APPARATUS USING THE SAME

(71) Applicant: Hitachi, Ltd., Tokyo (JP)

(72) Inventors: Kohjiro Iwasawa, Tokyo (JP); Takanori Nishiyama, Tokyo (JP); Kazuyuki Kato, Tokyo (JP); Hideta Habara, Tokyo (JP); Yosuke Otake, Tokyo (JP); Satoshi Yamashita, Tokyo (JP); Toru Shirai, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 32 days.

(21) Appl. No.: 17/078,308

(22) Filed: Oct. 23, 2020

(65) Prior Publication Data
US 2021/0278489 A1 Sep. 9, 2021

(30) Foreign Application Priority Data

Mar. 5, 2020 (JP) .................................. 2020-037856

(51) Int. Cl.
   *G01R 33/34* (2006.01)
   *G01R 33/3415* (2006.01)
   *A61B 5/055* (2006.01)

(52) U.S. Cl.
   CPC ........ *G01R 33/34084* (2013.01); *A61B 5/055* (2013.01); *G01R 33/34007* (2013.01); *G01R 33/3415* (2013.01); *G01R 33/34046* (2013.01)

(58) Field of Classification Search
   CPC ........ G01R 33/34084; G01R 33/34007; G01R 33/34046; G01R 33/3415; A61B 5/055
   See application file for complete search history.

(56) References Cited

U.S. PATENT DOCUMENTS 5,361,765 A * 11/1994 Herlihy ............ G01R 33/34046
                                                                324/318
5,370,118 A * 12/1994 Vij ..................... G01R 33/3678
                                                                324/318
(Continued)

FOREIGN PATENT DOCUMENTS

JP          2013244410 A          12/2013
JP          2014-73294 A           4/2014
                  (Continued)

OTHER PUBLICATIONS

Japanese Office Action received in corresponding Japanese Application No. 2020-037856 dated Jun. 27, 2023.
(Continued)

*Primary Examiner* — Dixomara Vargas
(74) *Attorney, Agent, or Firm* — Mattingly & Malur, PC

(57) ABSTRACT

Provided is a coil device capable of improving operability or durability thereof, being attached to a subject in a close contact state regardless of the size of a head of the subject, and obtaining a high-quality MRI image. The coil device includes at least one coil unit which has a coil element and a coil support portion which has a mechanism for attaching the coil unit to a head of a subject. The coil support portion includes a base portion, a support body which is connected to the base portion and has an elastic member, and a holder which connects the support body to the at least one coil unit and the holder has at least three contact points which are formed directly or indirectly with respect to the base portion.

19 Claims, 17 Drawing Sheets

(56) References Cited

U.S. PATENT DOCUMENTS

| | | | | |
|---|---|---|---|---|
| 6,784,665 B1* | 8/2004 | Chan | | G01R 33/34046 324/309 |
| 7,450,985 B2* | 11/2008 | Meloy | | A61G 7/072 128/870 |
| 7,911,209 B2* | 3/2011 | Alradady | | G01R 33/34076 324/309 |
| 9,645,207 B2* | 5/2017 | Taracila | | G01R 33/34084 |
| 9,884,200 B2* | 2/2018 | Pillutla | | A61N 2/02 |
| 10,004,423 B2* | 6/2018 | Driemel | | A61B 5/055 |
| 10,165,961 B2 | 1/2019 | Alagappan et al. | | |
| 10,827,948 B1* | 11/2020 | Tramm | | A61B 5/7405 |
| 10,852,372 B2 | 12/2020 | Iwasawa et al. | | |
| 2002/0077539 A1* | 6/2002 | Schmit | | A61B 6/0442 128/869 |
| 2004/0100346 A1* | 5/2004 | Jevtic | | G01R 33/34046 335/299 |
| 2007/0066885 A1* | 3/2007 | Vaughan | | G01R 33/283 324/318 |
| 2007/0285093 A1* | 12/2007 | Driemel | | G01R 33/34084 324/309 |
| 2008/0024133 A1* | 1/2008 | Vaughan | | G01R 33/3678 324/318 |
| 2009/0027053 A1* | 1/2009 | Decke | | A61B 5/055 324/318 |
| 2009/0306494 A1* | 12/2009 | Scarth | | G01R 33/341 378/63 |
| 2012/0286784 A1* | 11/2012 | Driemel | | G01R 33/34007 324/318 |
| 2013/0023756 A1* | 1/2013 | Driemel | | G01R 33/34046 600/422 |
| 2013/0076358 A1* | 3/2013 | Taracila | | G01R 33/34084 324/322 |
| 2013/0076361 A1* | 3/2013 | Taniguchi | | G01R 33/34092 324/322 |
| 2013/0131498 A1* | 5/2013 | Taracila | | G01R 33/34084 324/322 |
| 2013/0184563 A1* | 7/2013 | Driemel | | G01R 33/34007 600/415 |
| 2013/0317346 A1* | 11/2013 | Alagappan | | G01R 33/34046 600/415 |
| 2015/0057528 A1* | 2/2015 | Driemel | | G01R 33/34084 600/415 |
| 2015/0065852 A1* | 3/2015 | Driemel | | A61B 5/055 600/410 |
| 2016/0025823 A1* | 1/2016 | Driemel | | G01R 33/34007 600/422 |
| 2016/0077170 A1* | 3/2016 | Eberler | | A61B 5/055 324/321 |
| 2017/0119277 A1* | 5/2017 | Wu | | A61B 6/037 |
| 2018/0356477 A1* | 12/2018 | Lau | | A61B 5/055 |
| 2019/0277927 A1* | 9/2019 | Stickle | | A61B 5/0042 |
| 2020/0256937 A1* | 8/2020 | Iwasawa | | A61B 5/055 |
| 2021/0121066 A1* | 4/2021 | Rheineck | | A61B 5/0035 |
| 2021/0369133 A1* | 12/2021 | Coppens | | G01R 33/34084 |

FOREIGN PATENT DOCUMENTS

| | | |
|---|---|---|
| JP | 2015-98 A | 1/2015 |
| JP | 2019-216879 A | 12/2019 |
| WO | 2007/108190 A1 | 9/2007 |

OTHER PUBLICATIONS

Chinese Office Action received in corresponding Chinese Application No. 202011410279.2 dated Dec. 5, 2023.

* cited by examiner

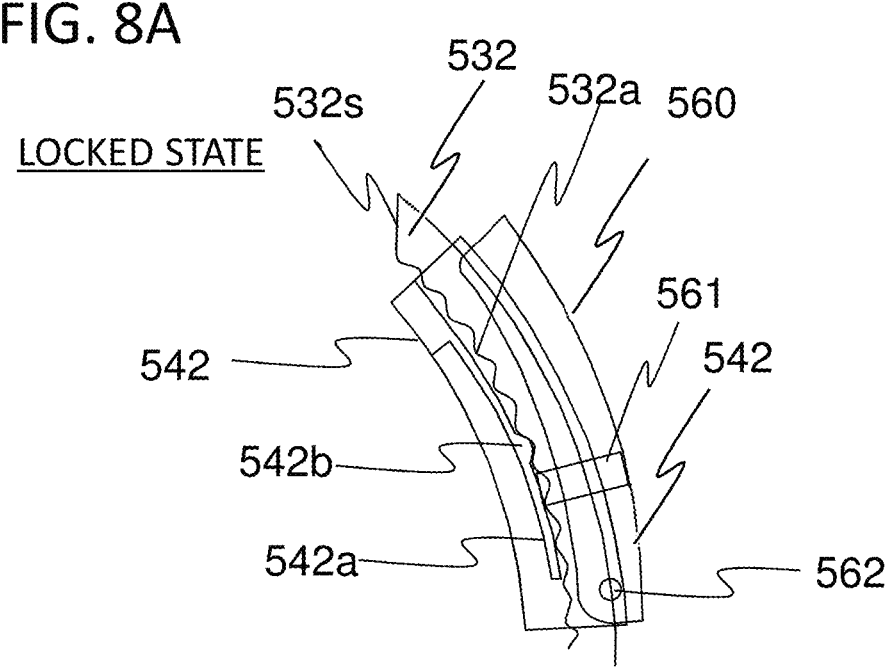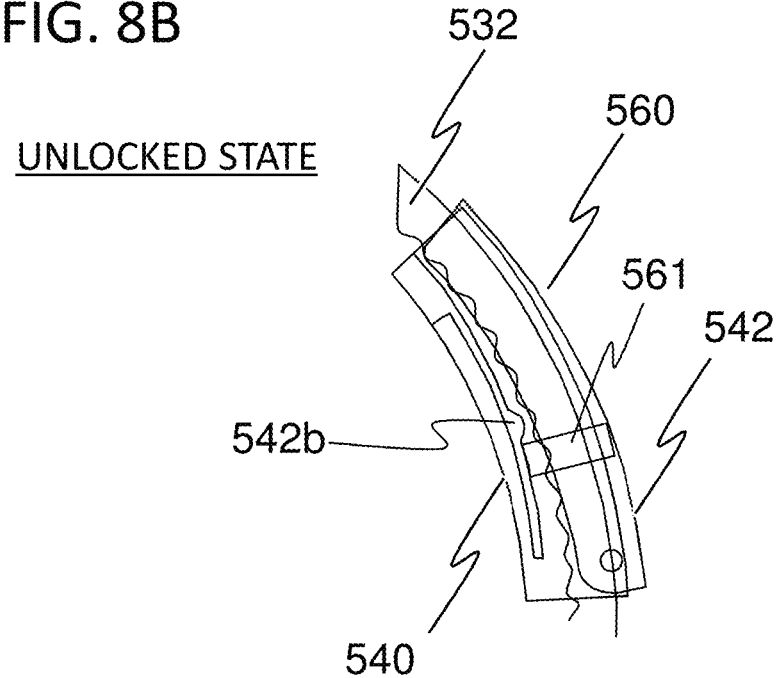

590

590

HEAD COIL DEVICE AND MAGNETIC RESONANCE IMAGING APPARATUS USING THE SAME

INCORPORATION BY REFERENCE

The present application claims priority from Japanese patent application JP-2020-037856 filed on Mar. 5, 2020, the content of which is hereby incorporated by reference in to this application.

BACKGROUND OF THE INVENTION

Field of the Invention

The present invention relates to a coil device which is used as a receiving coil or a transmitting coil of a magnetic resonance imaging apparatus (hereinafter, referred to as an MRI apparatus) and particularly to a head coil device which is attached to a subject with improved performance.

Description of the Related Art

An MRI apparatus is a medical image diagnostic apparatus that causes a magnetic resonance in a nuclear spin in an arbitrary cross-section crossing an inspection target and obtains a tomographic image in the cross-section from a generated nuclear magnetic resonance signal. The MRI apparatus is called a horizontal magnetic field type, vertical magnetic field type MRI apparatus, or the like according to a static magnetic field direction.

In MRI imaging, a subject placed in a static magnetic field is irradiated with a high-frequency magnetic field by a high-frequency coil while a gradient magnetic field is applied to the subject. The nuclear spin in the subject, for example, the nuclear spin of a hydrogen atom is excited by the irradiation of the high-frequency magnetic field and a circularly polarized magnetic field is generated as a nuclear magnetic resonance signal when the excited nuclear spin returns to equilibrium. This signal is detected by the high-frequency coil and is subjected to signal processing to image the distribution of hydrogen nuclei in a living body.

The high-frequency coil is largely classified into two coils, that is, a volume coil and a surface coil according to the shapes. In general, a volume coil which can uniformly irradiate a wide range is used as the high-frequency coil (transmitting coil) for irradiating the high-frequency magnetic field. On the other hand, a surface coil which can be disposed in the vicinity of the subject is used as the high-frequency coil (receiving coil) for detecting a signal. This is because the signal acquisition efficiency becomes higher and the image quality of the MRI image becomes higher as the distance between the high-frequency coil and the subject becomes smaller. A receiving coil fora head which is generally commercialized includes a coil housing having a fixed size with emphasis on durability. Meanwhile, a receiving coil for a head including a size changing mechanism is also under consideration (for example, see JP-A-2013-244410).

The general receiving coil for the head having a fixed size is designed for a large subject in order to increase population coverage. Therefore, there is a problem that the distance between the coil and the subject becomes large and the signal acquisition efficiency decreases for many subjects. Further, it takes time to fix the head of the subject to prevent deterioration of the image quality of the MRI image due to body movement. In general, a space between the coil housing and the subject is filled with a sponge in the fixing operation. In the operation of filling the sponge, a technician changes the number and shape of sponges according to the size of the head so that the fixing operation can be performed sufficiently. It is considered that a main reason why this operation time cannot be shortened is that the fixing operation needs to be performed in a narrow space between the coil housing and the subject. That is, it is considered that a structure in which a fixture (sponge in this case) and the receiving coil are spatially disposed in this order with respect to the subject is an essential problem that a fixing operation cannot be simplified.

JP-A-2013-244410 discloses the receiving coil for the head which can be changed in size and in which a plurality of coil receiving units are respectively supported by the support portions. However, since it takes effort when moving and fixing the position of each coil with respect to a plurality of support portions, there is a problem that operability is deteriorated. Further, when separating the coil, the coil fixed to each of the plurality of support portions needs to be released and moved to an open position. As a result, there is a problem that the subject cannot be released promptly. This is a serious problem especially when the subject is vomiting or when responding to an emergency. Further, since the coil receiving unit has a structure in which the coil is supported at one contact portion with the support portion, there is a problem that durability is deteriorated. When the structure is enlarged to have sufficient durability, operability is further deteriorated.

SUMMARY OF THE INVENTION

The invention has been made in view of the above-described circumstances and an object of the invention is to provide a high-quality MRI image regardless of the size of a head of a subject without deteriorating operability or durability.

In order to solve the above-described problems, a coil device of the invention holds a coil by a substantially T-shaped flexible holder and a support body supporting the holder slidably supports one portion of three ends of the T-shaped holder and supports the other two portions while maintaining the freedom of movement.

That is, a coil device of the invention is a head coil device used for an MRI apparatus including: at least one coil unit which has a coil element; and a coil support portion which has a mechanism for attaching the coil unit to a head of a subject, in which the coil support portion includes a base portion, a support body which is connected to the base portion and has an elastic member, and a holder which connects the support body to the at least one coil unit, and in which the holder has at least three contact points which are formed directly or indirectly with respect to the base portion.

According to the invention, since the holder supporting the coil attached to the subject is supported at three points of the base portion, the coil device capable of stably supporting a heavy coil with a simple structure is provided. Further, the coil unit fixed to the holder can be attached to the head of the subject by a simple operation in which the head of the subject is placed on the base portion and the holder is slid along the curved shape of the support body. Accordingly, since it is possible to improve the efficiency of MRI inspection by reducing the effort and burden when attaching the coil and to dispose the head and the coil in a close contact state, it is possible to improve the MRI image quality by increasing the receiving or transmitting sensitivity.

BRIEF DESCRIPTION OF THE DRAWINGS

FIG. 4A is a front view and FIG. 4B is a side view;

FIGS. 5A to 5C are diagrams respectively illustrating an array coil, a sub-coil constituting the array coil, and a transmission/reception magnetic coupling prevention circuit;

FIG. 7A is a side view and FIG. 7B is a front view;

FIGS. 8A and 8B are diagrams illustrating a lock mechanism portion for the holder and the support body at a front end thereof, where FIG. 8A illustrates a locked state and FIG. 8B illustrates an unlocked state;

FIG. 9A is a side view and FIG. 9B is a front view;

FIG. 11A is a diagram illustrating a state in which a coil is located at a retracted position and FIG. 11B is a diagram illustrating a coil attached state;

FIG. 13A is a diagram illustrating a coil attached state and FIG. 13B is a diagram illustrating a retracted state;

FIG. 14A illustrates an attached state, FIG. 14B illustrates an intermediate state between a coil attached state and a retracted state, and FIG. 14C illustrates a retracted state;

FIG. 17A is a circuit diagram of a sub-coil and FIG. 17B is a diagram illustrating a transmission/reception magnetic coupling prevention circuit.

DETAILED DESCRIPTION OF THE INVENTION

Hereinafter, embodiments of the invention will be described with reference to the drawings.

Embodiments of MRI Apparatus

Figure 1A:
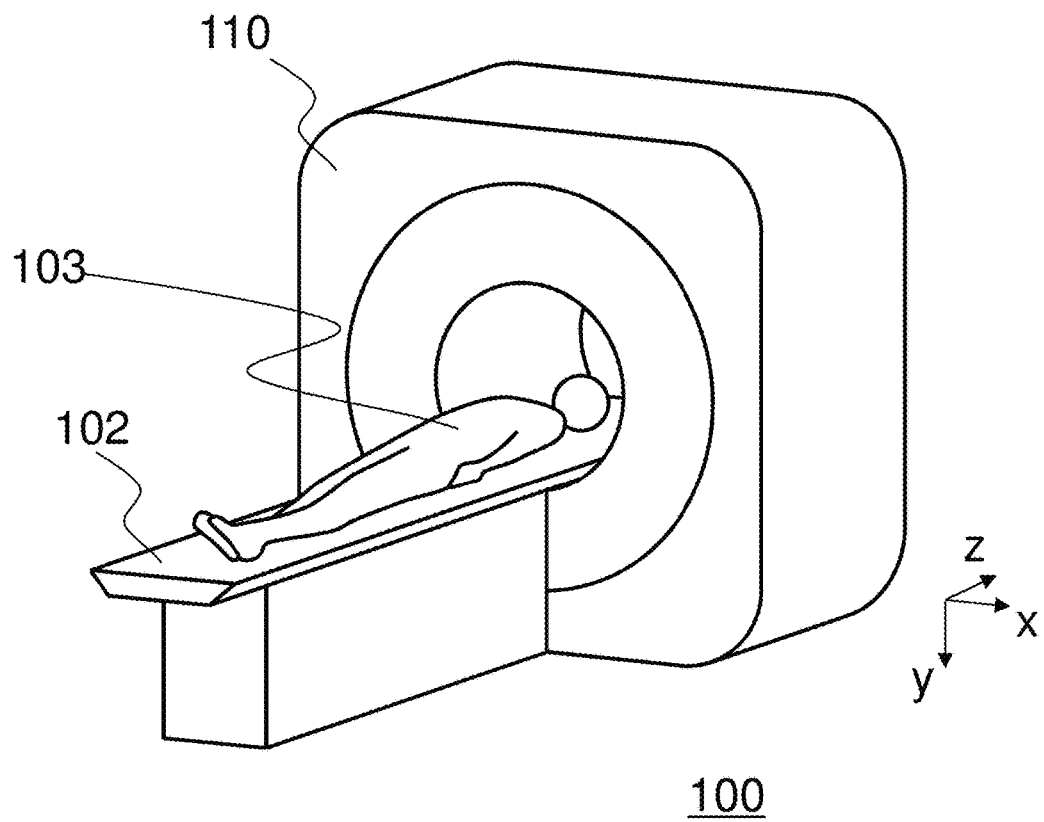
FIGS. 1A and 1B are respectively diagrams illustrating an appearance of an MRI apparatus according to the invention.
Figure 1B:
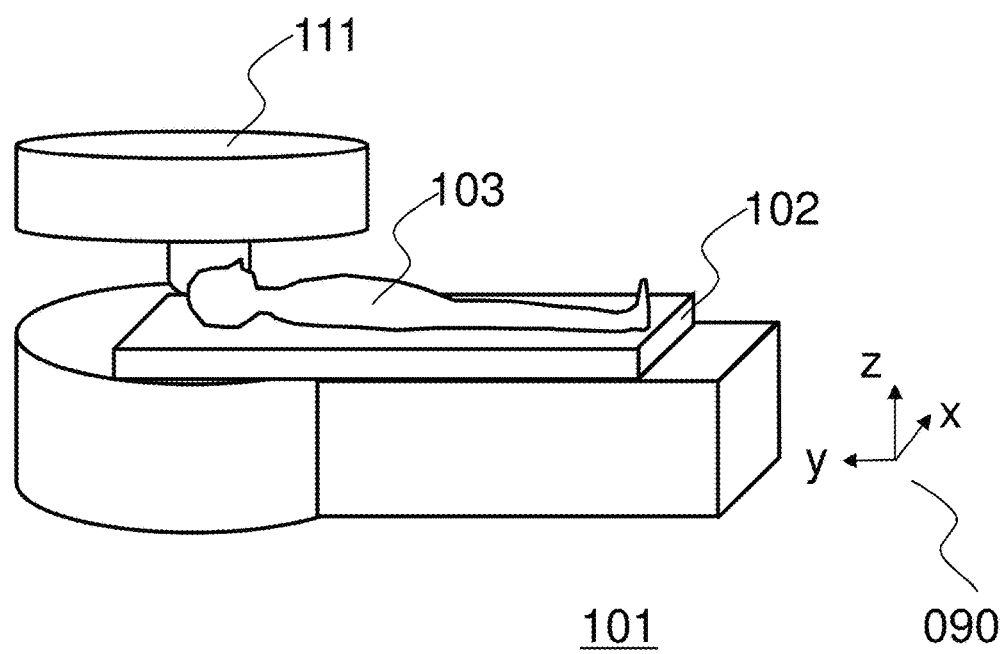

First, an overall configuration of an MRI apparatus according to the invention will be described with reference to FIGS. 1A, 1B, and 2. FIGS. 1A and 1B are diagrams illustrating an appearance of the MRI apparatus. FIG. 1A illustrates a horizontal magnetic field type MRI apparatus 100 using a tunnel magnet that generates a static magnetic field by a solenoid coil. FIG. 1B illustrates a hamburger type (open type) vertical magnetic field type MRI apparatus 101 in which magnets are separated into upper and lower parts to enhance a sense of openness. These MRI apparatuses 100 and 101 include a table 102 on which a subject 103 is placed. In the drawings, a static magnetic field direction is the z direction and two directions perpendicular thereto are respectively the x direction and the y direction.

This embodiment can be applied to both the MRI apparatus 100 including a horizontal magnetic field type magnet 110 and the MRI apparatus 101 including a vertical magnetic field type magnet 111. Further, the MRI apparatus of this embodiment is not limited to these modes and various known MRI apparatuses can be used regardless of the mode and type of the apparatus. Hereinafter, the horizontal magnetic field type MRI apparatus 100 will be described as an example.

Figure 2:
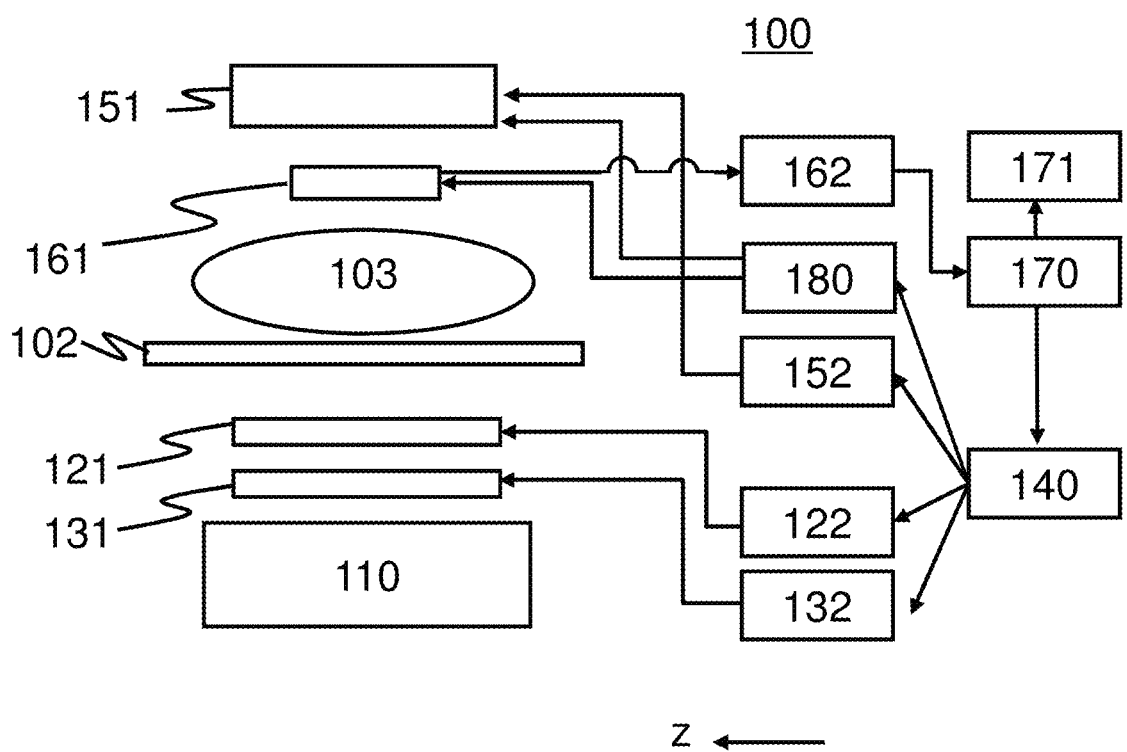
FIG. 2 is a block diagram of the MRI apparatus.

FIG. 2 is a block diagram illustrating a schematic configuration of the MRI apparatus 100. As illustrated in this drawing, the MRI apparatus 100 includes the horizontal magnetic field type magnet 110, a gradient magnetic field coil 131, an RF transmitting coil 151, an RF receiving coil 161, a gradient magnetic field power source 132, a SIMM coil 121, a SIMM power source 122, a high-frequency magnetic field generator 152, a receiver 162, a magnetic coupling prevention circuit driving device 180, a computer (PC) 170, a sequencer 140, and a display device 171. The subject 103 is disposed on the table 102 and is disposed in a static magnetic field space formed by the magnet 110.

The gradient magnetic field coil 131 is connected to the gradient magnetic field power source 132 and generates a gradient magnetic field. The SIMM coil 121 is connected to the SIMM power source 122 and adjusts the homogeneity of the magnetic field. The RF transmitting coil 151 is connected to the high-frequency magnetic field generator 152 and irradiates (transmits) a high-frequency magnetic field to the subject 103. The RF receiving coil 161 is connected to the receiver 162 and receives a nuclear magnetic resonance signal from the subject 103. The magnetic coupling prevention circuit driving device 180 is connected to a magnetic coupling prevention circuit. The magnetic coupling prevention circuit is a circuit which is connected to each of the RF transmitting coil 151 and the RF receiving coil 161 and prevents magnetic coupling between the RF transmitting coil 151 and the RF receiving coil 161.

The sequencer 140 sends a command to the gradient magnetic field power source 132, the high-frequency magnetic field generator 152, and the magnetic coupling prevention circuit driving device 180 to operate each of them. The command is sent according to the instruction from the computer (PC) 170. Further, a magnetic resonance frequency which is a detection reference is set by the receiver 162 according to the instruction from the computer (PC) 170. For example, the subject 103 is irradiated with a high-frequency magnetic field via the RF transmitting coil 151 according to the command from the sequencer 140. A nuclear magnetic resonance signal which is generated from the subject 103 by the irradiation of the high-frequency magnetic field is detected by the RF receiving coil 161 and is detected by the receiver 162.

The computer (PC) 170 also functions as a signal processing unit that controls the overall operation of the MRI apparatus 100 and performs various signal processing. For example, a signal detected by the receiver 162 is received via an A/D converting circuit and is subjected to signal processing such as image reconstruction. The result is displayed on the display device 171. The detected signal or the measurement condition is stored in a storage medium if necessary. Further, a command is sent to the sequencer 140 so that each device is operated at a preprogrammed timing and strength. Further, when it is necessary to adjust the static magnetic field homogeneity, the sequencer 140 sends a command to the SIMM power source 122 to cause the SIMM coil 121 to adjust the magnetic field homogeneity.

Figure 3:
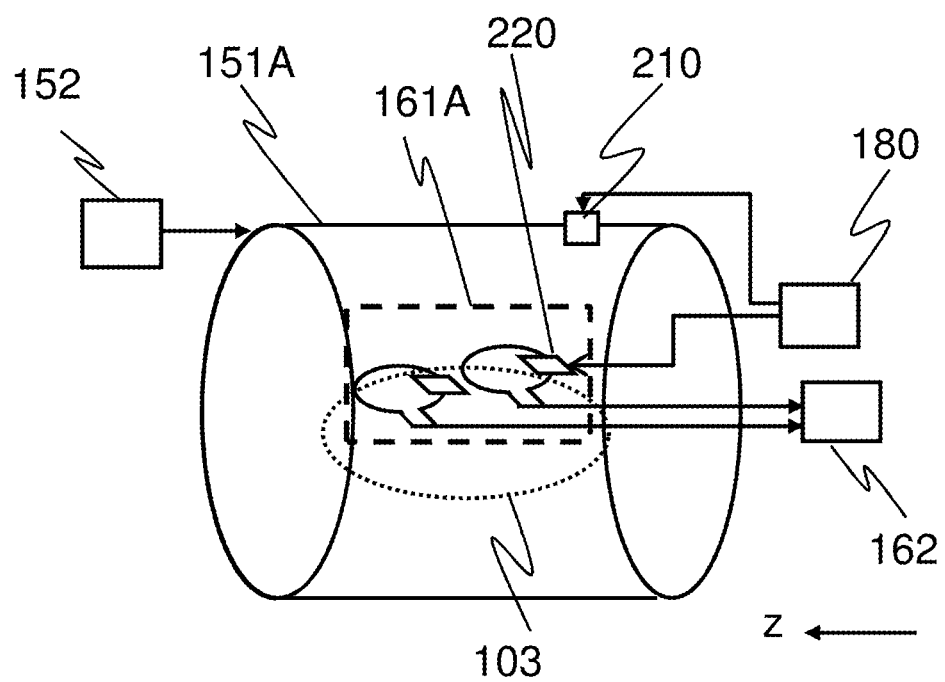
FIG. 3 is a diagram showing a relationship between an RF transmitting coil and an RF receiving coil of the MRI apparatus.

Next, the RF transmitting coil 151 and the RF receiving coil 161 of this embodiment will be described in detail with reference to FIG. 3. FIG. 3 shows an example in which an RF coil (birdcage type RF coil) 151A having a birdcage shape is used as the RF transmitting coil 151 and an array coil 161A obtained by arranging a plurality of RF coils (surface coils) having a loop shape is used as the RF receiving coil 161. Further, FIG. 3 shows two surface coils (sub-coils) constituting the array coil 161A, but the number of the sub-coils may be three or more or one.

The resonance frequency of the birdcage type RF coil 151A used as the RF transmitting coil 151 is adjusted to the resonance frequency of the element to be excited, for example, the magnetic resonance frequency of the hydrogen nucleus capable of exciting the hydrogen nucleus. The array coil 161A used as the RF receiving coil 161 is adjusted to detect the nuclear magnetic resonance signal of the element which can be excited by the birdcage type RF coil 151A.

Further, as shown in FIG. 3, the birdcage type RF coil 151A is disposed so that its axis is coaxial with the center axis of the magnet 110 and the array coil 161A is disposed in the birdcage type RF coil 151A. The birdcage type RF coil 151A is connected to the high-frequency magnetic field generator 152 and the array coil 161A is connected to the receiver 162.

Further, the birdcage type RF coil 151A includes a magnetic coupling prevention circuit 210 which prevents magnetic coupling with the array coil 161A. This magnetic coupling prevention circuit 210 is a circuit that prevents magnetic coupling between the RF transmitting coil (the birdcage type RF coil 151A) and the RF receiving coil (the array coil 161A) and is called a transmission/reception magnetic coupling prevention circuit 210. The transmission/reception magnetic coupling prevention circuit 210 is inserted in series into a straight conductor of the birdcage type RF coil 151A.

The array coil 161A includes a magnetic coupling prevention circuit 220 which prevents magnetic coupling with the birdcage type RF coil 151A. The magnetic coupling prevention circuit 220 is also a transmission/reception magnetic coupling prevention circuit which prevents magnetic coupling between the RF transmitting coil (the birdcage type RF coil 151A) and the RF receiving coil (the array coil 161A). The transmission/reception magnetic coupling prevention circuit 220 is inserted in series into each surface coil constituting the array coil 161A.

The magnetic coupling prevention circuit driving device 180 is connected to each of the transmission/reception magnetic coupling prevention circuit 210 and the transmission/reception magnetic coupling prevention circuit 220. The transmission/reception magnetic coupling prevention circuit 210 allows the array coil 161A to receive a magnetic resonance signal by preventing magnetic coupling with the array coil 161A or irradiating an RF magnetic field of a resonance frequency using the birdcage type RF coil 151A, for example, in such a manner that a PIN diode becomes an ON state or an OFF state according to a control signal by a circuit including a PIN diode turned on or off by a control signal from the magnetic coupling prevention circuit driving device 180. The array coil 161A will be described in detail later.

Although FIG. 3 shows a case in which the array coil 161A is the RF receiving coil, a birdcage type RF coil 300 may be used as an RF transmitting coil for a whole body and the array coil 161A may be separately used as an RF transmitting coil for a local part. In this case, in FIG. 3, the array coil 161A is connected to the high-frequency magnetic field generator 152 and an RF receiving coil different from the array coil 161A is disposed. Alternatively, in some cases, a transmission/reception switch is connected between the high-frequency magnetic field generator 152 and the receiver 162 and the array coil 161A is used as an RF coil for both transmission and reception.

In any case, after the array coil 161A is attached on an inspection site of the subject 103 and is disposed in a static magnetic field space, imaging is started according to a preset inspection protocol.

The coil device of the invention is a head coil device used when the inspection site includes a head of a subject and has a structure in which the operability when attaching the array coil 161A onto the subject is improved and the adhesion to the subject is improved. Hereinafter, an embodiment of the head coil device will be described.

Embodiment of Head Coil Device

First Embodiment

In this embodiment, a case in which the head coil device is an RF receiving coil that receives an NMR signal will be described.

The head coil device (simply also referred to as a coil device) mainly includes a coil unit which is attached to be in close contact with a head of a subject and a coil support portion which supports the coil unit. The coil support portion includes a base portion, a holder holding the coil unit, and a support body supporting the holder with respect to the base portion, and has a mechanism which makes the coil unit be in close contact with the head of the subject. Hereinafter, the mechanism of the coil support portion and the coil unit will be described.

[Coil Unit]

Figure 4A:
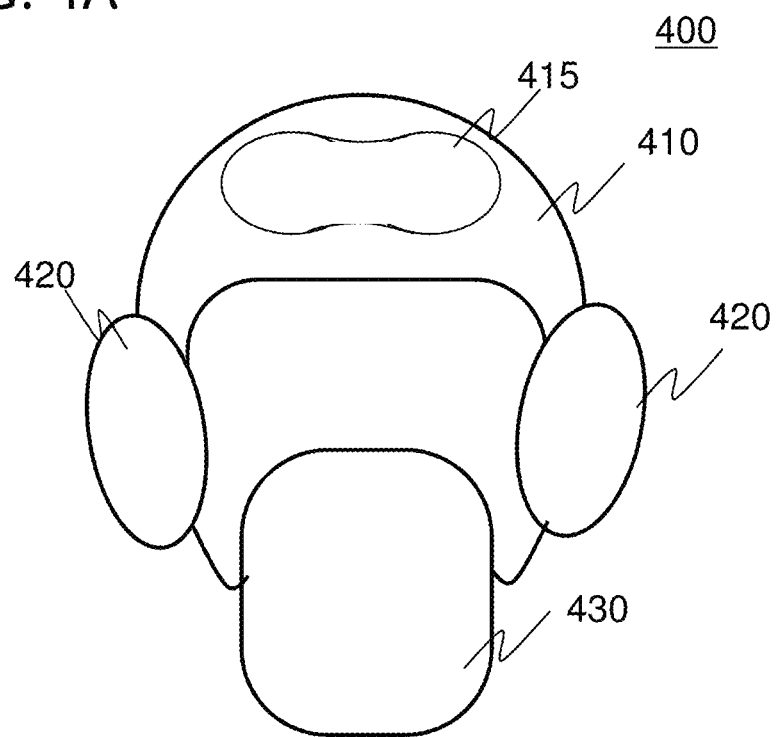
FIGS. 4A and 4B are diagrams illustrating an outline of a coil unit of a coil device of a first embodiment, where
Figure 4B:
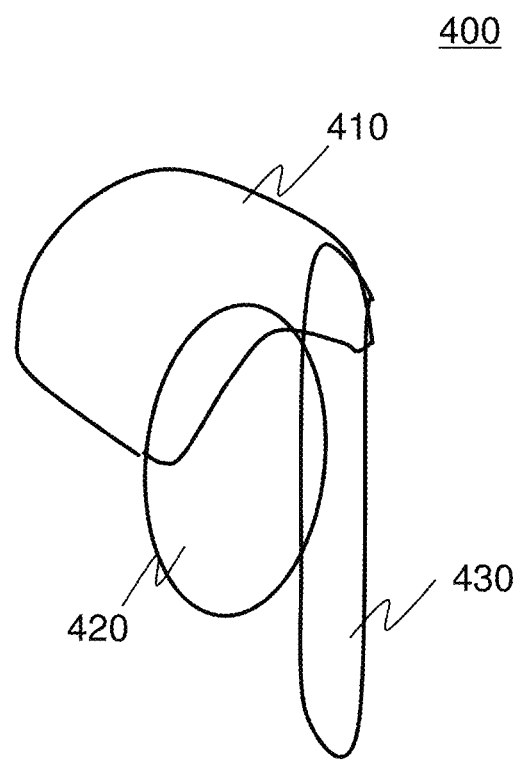

The coil device of this embodiment includes at least one or more coil units 400 which include a coil unit covering a head (front head). Specifically, as illustrated in FIGS. 4A and 4B, the coil units may include a coil unit (a first coil unit) 410 which covers only a head (a front head) and further include any one or both of a coil unit (a second coil unit) 420 which covers a portion extending from the ear to the neck of the subject and a coil unit (a third coil unit) 430 which covers from the occipital region to the vicinity of the scapula. In the description below, for convenience, the first coil unit 410 is referred to as a face coil, the second coil unit 420 is referred to as a side coil, and the third coil unit 430 is referred to as a rear coil. However, these names do not limit the function of each coil unit. Further, when the coil units are not particularly distinguished, they may be collectively referred to as coil units.

The coil unit 400 basically includes a circuit portion which includes a coil loop formed of a conductor and an adjusting element such as a condenser or a capacitor for adjusting the resonance frequency and a cover member that covers the circuit portion. A part of the circuit portion is formed on a flexible printed circuit board and a flexible cable to be connected to the receiver 162 (FIG. 3) is connected thereto.

Figure 5A:
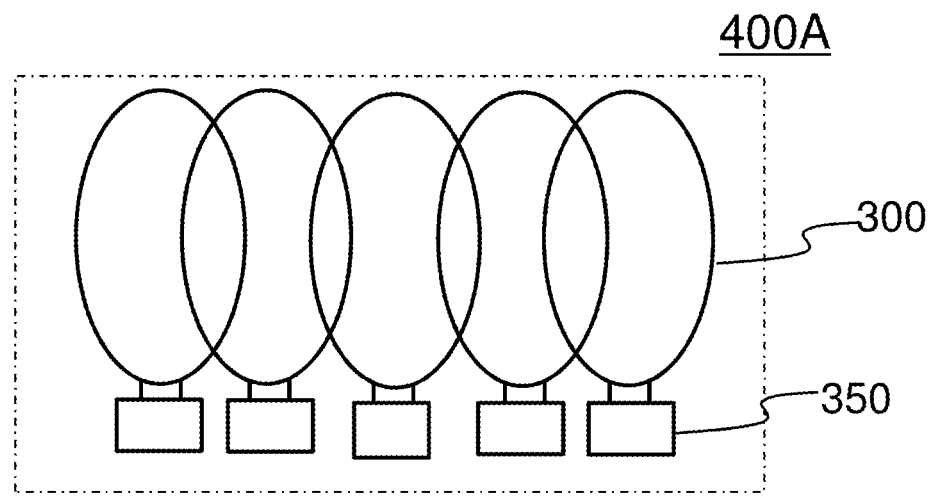
FIGS. 5A to 5C are diagrams illustrating an outline of a circuit of the coil unit of the first embodiment, where
Figure 5B:
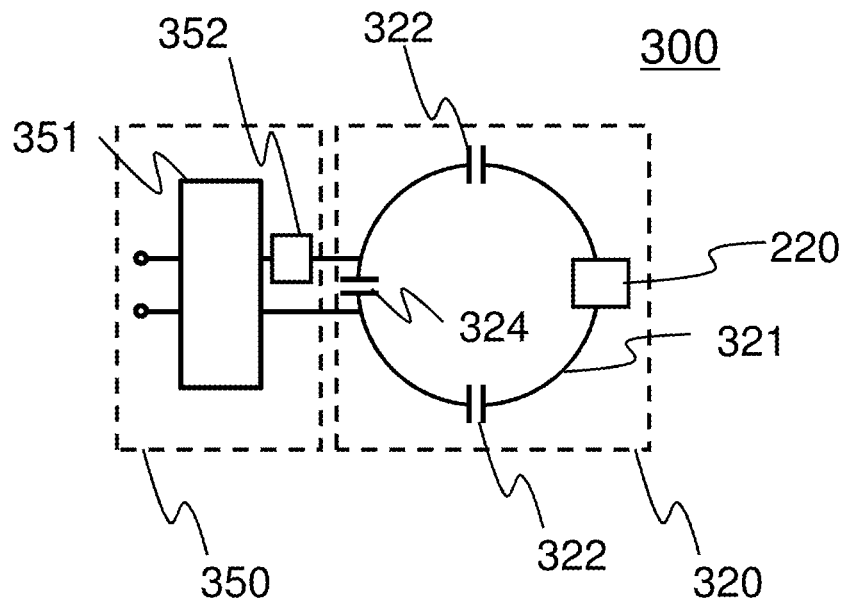
Figure 5C:
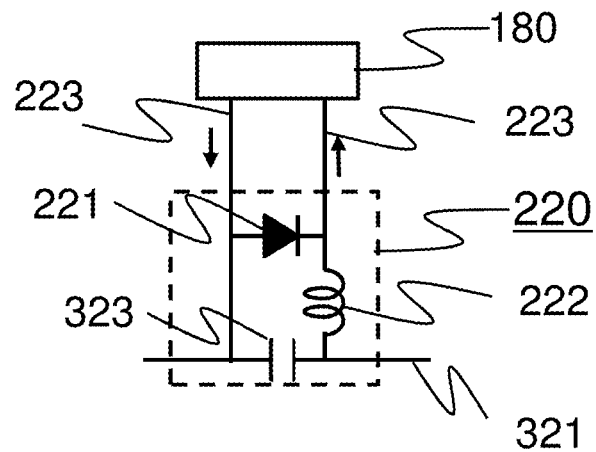

First, the circuit portion of the coil unit 400 will be described with reference to FIGS. 5A to 5C. As illustrated in FIG. 5A, an array coil 400A constituting the coil unit 400 has a configuration in which one or more sub-coils 300 are arranged in planar shape along the shape of the inspection target. Here, an example in which the sub-coils 300 are arranged in series is shown, but the sub-coils may be arranged two-dimensionally according to the shape of the inspection target. FIG. 5B is a diagram illustrating an example of the circuit portion of one sub-coil 300 of such an array coil 400A. As illustrated in FIG. 5B, the circuit portion includes a loop coil unit 320 which receives a nuclear magnetic resonance signal and a power supply board unit 350. The power supply board unit 350 includes a low (input) impedance signal processing circuit 351 and a magnetic coupling adjusting unit 352 which connects the loop coil unit 320 to the low impedance signal processing circuit 351. The magnetic coupling adjusting unit 352 includes at least one of a capacitor and an inductor.

A loop 321 of the loop coil unit 320 is formed by a conductor. Then, the first loop coil unit 320 includes a capacitor 324 which is connected in series to an inductor component of the loop 321. This inductor component and the capacitor 324 constitute a parallel resonance circuit. This capacitor 324 is referred to as a parallel capacitor in order to be distinguished from the other capacitor.

Further, a capacitor 322 which adjusts a resonance frequency and the transmission/reception magnetic coupling prevention circuit 220 (see FIG. 3) are inserted in series into the loop 321. This capacitor 322 is referred to as a series capacitor in order to be distinguished from the other capacitor. Additionally, a case in which two series capacitors 322 are provided is exemplified herein, but the number of the series capacitors 322 may be one or more.

In this way, the sub-coil 300 includes the magnetic coupling adjusting unit 352, the series capacitor 322 which is inserted in series with respect to the inductor component of the loop 321, and the parallel capacitor 324 which is inserted in series with respect to the inductor component so that the loop coil unit 320 functions as a parallel resonance circuit, as adjusting circuit elements.

One terminal of the low impedance signal processing circuit 351 on the side of the loop coil unit 320 is connected to one end of the parallel capacitor 324 of the loop coil unit 320 via the magnetic coupling adjusting unit 352. The other terminal of the low impedance signal processing circuit 351 on the side of the loop coil unit 320 is directly connected to the other end of the parallel capacitor 324 of the loop coil unit 320. The other terminal of the low impedance signal processing circuit 351 which is not on the side of the loop coil unit 320 is connected to the receiver 162 (FIG. 3) via a transmission cable.

The transmission/reception magnetic coupling prevention circuit 220 removes magnetic coupling with the birdcage type RF coil 151A which is the RF transmitting coil 151. The transmission/reception magnetic coupling prevention circuit 220 includes, as illustrated in FIG. 5C, a PIN diode 221, an inductor 222, and a control signal line 223.

The PIN diode 221 and the inductor 222 are connected in series to each other and are connected in parallel to a capacitor 323. Additionally, the capacitor 323 is a capacitor which is inserted into the loop 321. Further, the control signal line 223 is connected to both ends of the PIN diode 221. Then, the control signal line 223 is connected to the magnetic coupling prevention circuit driving device 180. A choke coil for preventing the mixing of high frequencies is inserted into the control signal line 223 (not illustrated). The inductor 222 and the capacitor 323 are adjusted to resonate in parallel at the frequency of the received nuclear magnetic resonance signal.

The parallel resonance circuit generally has a characteristic in which high impedance (high resistance) is obtained at the resonance frequency. Accordingly, when a current flows to the PIN diode 221, the PIN diode 221 is turned on and the capacitor 323 of the loop 321 resonates in parallel with the inductor 222 at the frequency of the received nuclear magnetic resonance signal to be a high impedance state. Thus, a part of the loop coil unit 320 has high impedance to be an open state at the frequency of the received nuclear magnetic resonance signal and the sub-coil 300 including the loop coil unit 320 also becomes an open state.

In this way, since the PIN diode 221 is turned on when a current flows thereto, the magnetic coupling between each sub-coil and the birdcage type RF coil 151A is removed. Thus, the magnetic coupling between the birdcage type RF coil 151A and the array coil 161A (400A) in which each sub-coil is a coil element is also removed.

Additionally, the number of the transmission/reception magnetic coupling prevention circuits 220 inserted into the sub-coil 300 is not limited thereto. Two or more transmission/reception magnetic coupling prevention circuits may be inserted into each loop 321. The magnetic coupling can be sufficiently reduced by inserting a plurality of transmission/reception magnetic coupling prevention circuits.

Further, the configuration of the transmission/reception magnetic coupling prevention circuit 220 is not limited to the above-described configuration. For example, a cross diode (not illustrated) may be used instead of the PIN diode 221. Accordingly, when a large signal flows to a conductor constituting the loop 321, the cross diode is turned on and the capacitor 323 of the loop 321 resonates in parallel with the inductor 222 at the frequency of the received nuclear magnetic resonance signal to be a high impedance state. In this case, the magnetic coupling prevention circuit driving device 180 may not be provided.

Next, a mechanical characteristic of the coil unit 400 including the circuit portion will be described. Hereinafter, the face coil 410 which is in close contact with various sizes of heads will be mainly described.

In the circuit portion of the face coil 410, for example, a portion formed by a conductor loop, a flexible printed board, or a flexible cable has flexibility. Further, a cover member that covers the circuit portion is formed of a resin material having excellent heat resistance and mechanical strength, such as fiber reinforced plastic (FRP) and elastomer, and has flexibility. The face coil 410 is formed of, for example, two thin resin materials manufactured by vacuum molding and is manufactured by sandwiching the loop portion and the board portion and forming a watertight structure with an adhesive around the periphery. A cable (not illustrated) that comes out of the circuit portion is made to come out from an upper portion that corresponds to the top of the subject, for example, so that the curvature of bending does not suddenly increase.

The face coil 410 with such a structure has flexibility as a whole, maintains its outer shape when an external force is not applied thereto, and is deformed when an external force is applied thereto, so that the face coil can be in close contact with the heads of the subjects of various head sizes. Further, the shape can be maintained by using the flexibility of the resin in the elastic deformation range. Furthermore, since it has a watertight structure, it is possible to prevent the intrusion of vomiting substances, cleaning chemicals and the like.

Further, although it is not essential, the face coil 410 includes a portion (FIG. 4A: a transmissive portion 415) that transmits light as a preferable structure. Since the face coil 410 covers more than half of the face of the subject when the face coil is attached to the subject, the field of view of the subject is closed. However, when the transmissive portion 415 through which light is transmitted is provided at the position of the face coil 410 that is placed in the eye of the subject at the time of the attaching operation, the field of view can be ensured and the anxiety of the subject can be relieved.

As the transmissive portion 415, in this embodiment, the conductor shape of the face coil 410 disposed in the eye of the subject is made into a frame of a sunglasses shape to form an opening. The opening may be just used as the transmissive portion 415, but the opening may be covered with a transmissive member to form the transmissive portion 415. As the material of the transmissive portion 415, for example, a transparent plastic can be used and an oxygen permeable plastic is particularly preferable. Such a member can be used as the transmissive portion 415 in such a manner that the member is sutured or adhered to the opening or removably fitted thereto.

The viewing angle in the right and left direction of the field of view provided by the transmissive portion 415 is preferably, for example, 90° or more and can be set to 180° by widening the opening. Since the face coil 410 of this embodiment can be disposed in a close contact state even for various head sizes, the field of view is improved particularly for a small subject.

[Coil Support Portion]

Next, a mechanism for supporting the coil unit 400 including the face coil 410 and a mechanism for bringing the coil unit 400 into close contact with the subject will be described. First, a basic structure of a coil support portion 500 supporting the face coil 410 will be described with reference to FIGS. 6, 7A, and 7B.

Figure 6:
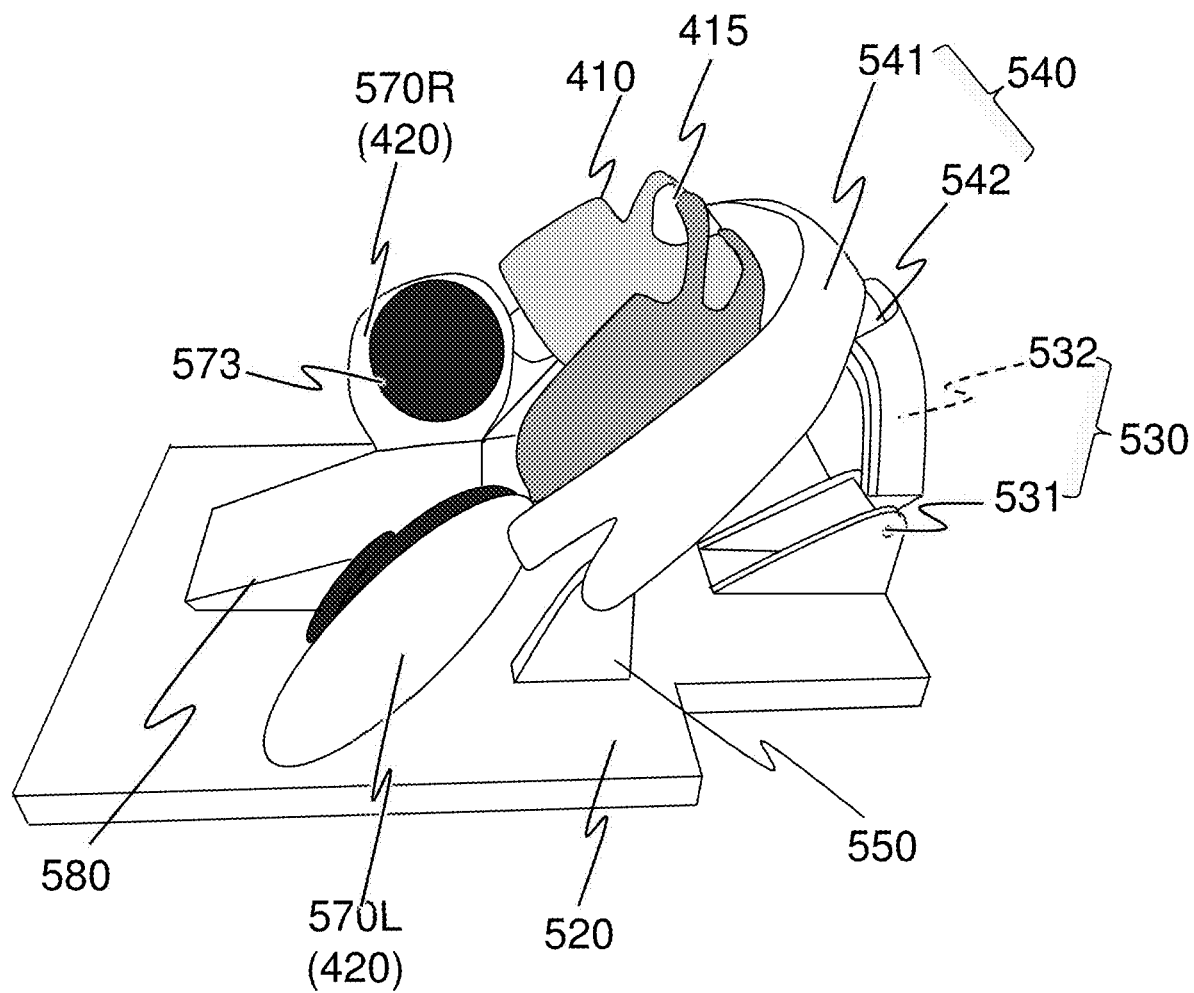
FIG. 6 is a diagram in which the coil device of the first embodiment is viewed from a side.
Figure 7A:
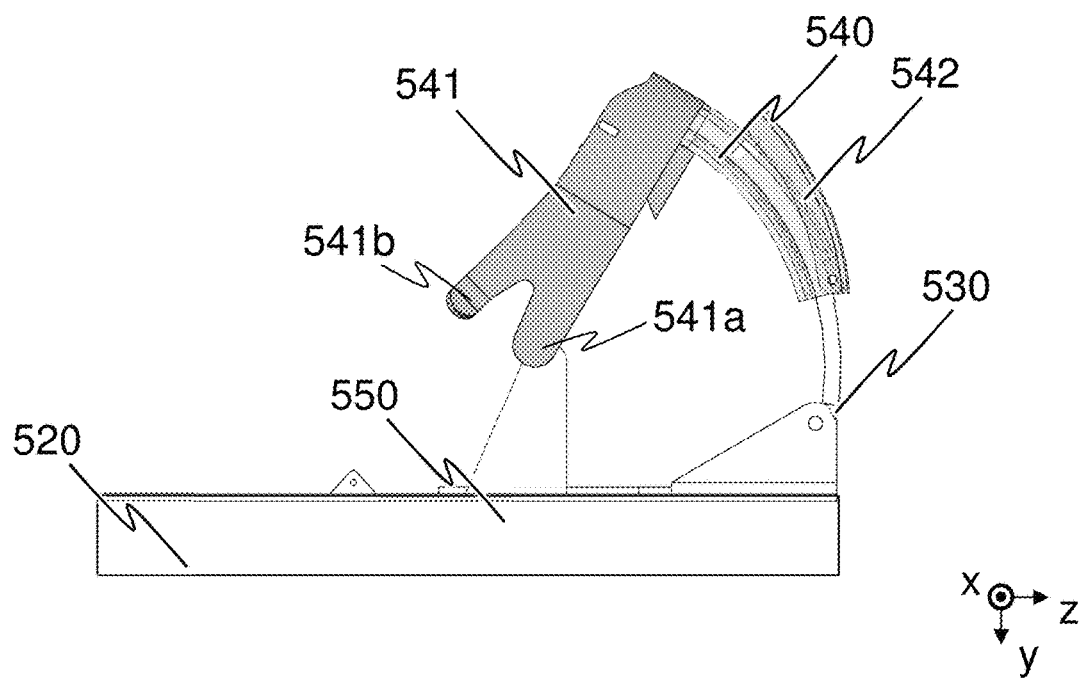
FIGS. 7A and 7B are diagrams showing a relationship between a support body and a holder of the coil device of the first embodiment, where
Figure 7B:
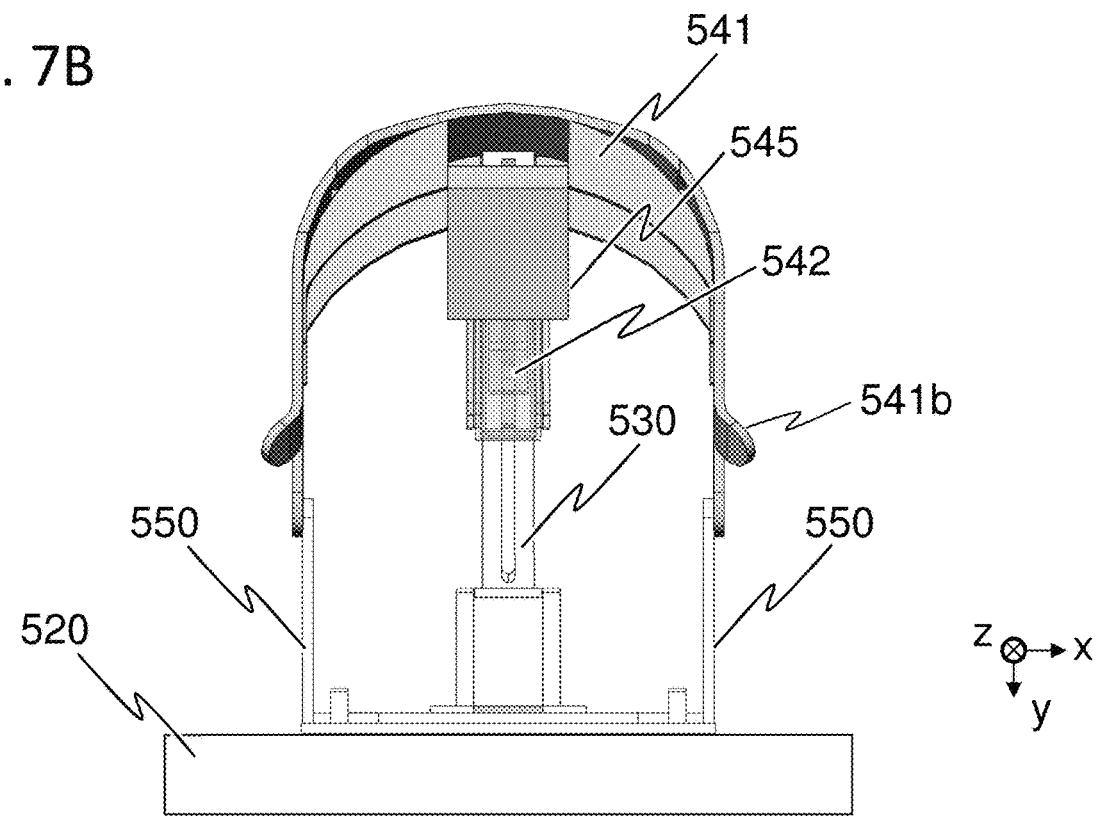

As illustrated in FIG. 6, the coil support portion 500 includes a base portion 520, a support body 530 of which one end is fixed to the base portion 520, a holder 540 which is slidable on the other end side of the support body 530, and a guide portion 550 which is fixed to the base portion 520 and comes into surface contact with the end of the holder 540 to support the holder 540 as basic constituting elements. The holder 540 has a shape in which two curved portions, that is, a first holder portion 541 and a second holder portion 542 are connected to each other in a T shape according to the shape of the face coil 410. The second holder portion 542 is curved so as to draw an arc about an axis substantially parallel to the right and left direction of the subject as shown in FIG. 7A and the first holder portion 541 is curved in the right and left direction of the subject about an axis orthogonal to the curve axis of the second holder portion 542 as shown in FIG. 7B. The second holder portion 542 is supported by the support body 530 and the right and left ends 541a of the first holder portion 541 come into surface contact with the guide portion 550.

In this way, in the coil support portion 500, the holder 540 having the face coil 410 fixed thereto is formed in a T shape, is slidably supported by the support body 530, and is supported by the guide portion 550 at both ends, a relatively heavy coil unit can be supported with a simple configuration and a stable attaching operation to the subject can be performed as will be described later.

Hereinafter, an embodiment of a structure of each part of the coil support portion 500 will be described. Further, in the following description, the right and left direction (horizontal direction) of the subject to which the face coil 410 is attached is the X direction, the front and back direction (vertical direction) is the Y direction, and the up and down direction (longitudinal direction) is the Z direction. Although these directions are not limited thereto, the coil device is disposed so that the Z direction matches the static magnetic field direction of the MRI apparatus when the MRI apparatus is a horizontal magnetic field apparatus illustrated in FIG. 1A.

The base portion 520 is a flat plate-shaped member in which the Y direction is a thickness direction and the head of the subject is disposed on the upper surface thereof. In the base portion 520, the support body 530 is fixed to a position corresponding to the rear side of the head and the thin plate-shaped guide portions 550 are fixed to both sides with the head interposed therebetween. Although it is not essential, a head support portion 580 may be fixed to a plate surface with which the head of the subject comes into contact.

The support body 530 can be formed of an elastic resin such as polyacetal resin (POM) and includes a portion (fixed portion) 531 which is fixed to the base portion 520 and a portion (curved portion) 532 which extends to the upper side of the fixed portion in a curved shape. In the example illustrated in FIG. 6, the fixed portion 531 and the curved portion 532 are integrally formed and are fixed to a support body fixed member that is fixed to the base portion 520. The second holder portion 542 of the holder 540 is slidably connected to the portion (curved portion) 532 having a curved shape. The curve of the curved portion 532 follows the curve of the second holder portion 542 and the second holder portion 542 can slide in a curved shape. The portion 531 fixed to the base portion 520 of the support body 530 has a structure having mechanical elasticity such as a leaf spring. Furthermore, the leaf spring portion may be a separate component. In this case, since only the leaf spring portion can be replaced, maintenance can be simplified.

The support body 530 can ensure the movement amount in the Y direction of the holder 540 supported by the support body 530 due to the elasticity of the material and the mechanical elastic structure of the fixed portion 531. That is, since the support body 530 is formed as an elastic member, the support body is movable in the vertical movable range (for example, 60 mm) for various head sizes without a complicated mechanism. Further, in the retracted state of the coil, the center of gravity is less likely to apply a load to the leaf spring portion of the support body 530 and creep can be prevented. Further, since the support body 530 has a curvature, the standby state can be realized with a minimum space on the parietal side.

At the time of performing the attaching operation, the face coil 410 can be in close contact with the subject, for example, in such a manner that the holder 540 is operated in the up and down direction (the Y direction) according to the size of the head of the subject while or after moving the holder 540 along the arc of the curved portion 532. In a state in which the subject does not exist, even when the face coil 410 is pressed downward at any position by performing the same operation, the face coil does not interfere with the head support portion 580. Further, when a fixing belt to be described later is used to improve the close contact state, the close contact of the face coil 410 is instantly released by the elastic force of the support body 530 if the fastening of the fixing belt is released.

Next, a connection mechanism between the support body 530 and the holder 540 will be described.

In this embodiment, as a mechanism for slidably connecting the holder 540, there is provided a mechanism (560 or the like) that adopts a structure in which the second holder portion 542 is formed as a hollow cylindrical shape and the curved portion 532 is fitted thereinto so that the movement of the holder 540 is locked or unlocked. An example of the lock mechanism will be described with reference to FIGS. 8A and 8B.

As illustrated in FIG. 8A, a rack and pinion mechanism is provided in the inner wall of the second holder portion 542 having a cylindrical shape and the curved portion 532 of the support body 530 that is in contact with the inner wall. Specifically, the inner wall of the second holder portion 542 is provided with a spring piece 542a and the spring piece 542a is provided with a protrusion portion 542b which engages with a rack portion 532a of the curved portion 532. When the protrusion portion 542b engages with the rack portion 532a, the movement of the second holder portion 542 is locked.

Further, a handle 560 having a push pin 561 fixed thereto is fixed to the holder 540 (the second holder portion 542) so as to be rotatable about a shaft 562. The push pin 561 penetrates to the inside of the second holder portion 542 and the end surface thereof comes into contact with the spring piece 542a of the inner wall of the second holder portion 542. As illustrated in FIG. 8B, when the operator grips the handle 560 and rotates the handle 560 about the shaft 562, the push pin 561 pushes the spring piece 542a downward to release the engagement between the protrusion portion 542b and the rack portion 532a. That is, the locked state of FIG. 8A is released so that the second holder portion 542 can slide smoothly.

When the operator releases the handle 560, the handle 560 returns to the state of FIG. 8A and the protrusion portion 542b of the second holder portion 542 engages with the rack portion 532a of the curved portion 532 so that the movement of the second holder portion 542 is locked. With such a locking and unlocking mechanism, the holder 540 can be moved to an arbitrary position according to the subject and be fixed at that position.

Additionally, the mechanism illustrated in FIGS. 8A and 8B is an example of the slidable connecting mechanism and the locking/unlocking mechanism and the coil device of this embodiment is not limited to this structure. For example, a mechanism in which a guide groove is provided at one side, a protrusion portion engaging with the guide groove is provided at the other side to be slidable, a notched recess is provided in the guide groove in a direction orthogonal to the slide direction, and the protrusion portion is fitted to the notched recess to lock the sliding movement or the like can be adopted.

Next, the holder 540 having the coil unit 400 fixed thereto will be described in detail with reference to FIGS. 7A and 7B again. Similarly to the support body 530, the holder 540 is preferably formed of an elastic resin (flexible material) such as POM and includes, as shown in FIGS. 7A and 7B, the first holder portion 541 which is curved in a semi-circular shape and the second holder portion 542 which is connected to the center thereof and is curved backward. These two parts may be formed by connecting separate members or can be formed by integral molding.

A block member 545 for fixing the coil unit 400 (here, the face coil 410) is fixed to the center of the first holder portion 541. The face coil 410 is fixed to the block member 545 with screws, an adhesive, or the like. Alternatively, the face coil 410 may be attachable to or detachable from the block member 545. As shown in FIG. 7A, both ends of the first holder portion 541 are bifurcated and one end 541a is pressed against the guide portion 550 by the elasticity of the holder 540 so as to be supported by the guide portion 550. As shown in FIG. 7B, the other end 541b has a shape opened to the outside and has a function (interlocking opening/closing function) of moving a side panel to which the side coil (the second coil unit) to be described later is fixed from the retracted state to the close contact state.

As described above, the second holder portion 542 is a cylindrical member with which the curved portion 532 of the support body 530 engages and is connected to the rear side of the portion to which the block member 545 of the first holder portion 541 is fixed.

The holder 540 can attach the face coil 410 fixed to the holder 540 to the subject just by sliding the second holder portion 542 along the curved portion 532 with respect to the support body 530. At this time, since the holder 540 (the front end of the first holder portion 541) is in contact with the guide portion 550, it is possible to prevent damage due to the horizontal twisting and to improve durability. Further, for example, even when the subject accidently leans against the holder 540 so that a force is applied to press the holder 540 downward (the +Y direction), the right and left lower ends of the first holder portion 541 directly contact the base portion 520 and serve as a stopper that prevents the damage of the face coil 410. Since the holder 540 serves as a protector that prevents the breakage from the right and left sides of the face coil 410, durability is improved. Particularly, this advantage is effective when the face coil 410 is flexible.

Next, a configuration of the coil support portion associated with the side coil (the second coil unit) 420 will be described.

Similarly to the face coil 410, the side coil 420 includes a circuit portion (FIGS. 5A to 5C) which includes a coil loop conductor and an adjusting element thereof and a cover member that covers the circuit portion and is fixed to each of a pair of right and left side panels (side panel portions) 570L and 570R as illustrated in FIG. 6.

Since the structures of the right and left side panels 570L and 570R are the same except for the difference between the right and left sides, they will be described as a side panel 570 when they are not distinguished from each other. As illustrated in black in FIG. 6, a cushioning material 573 such as a sponge may be fixed to the side coil 420 fixed to the side panel 570. Accordingly, the close contact state with the subject is improved, the sound deadening or soundproofing effect is obtained, and the coil can be attached while the subject attaches soundproof headphones or the like thereto. Further, the side panel 570 is at least partially formed of a flexible material and the side coil 420 can be in close contact with the subject.

The side panel 570 is attached to the shaft fixed to the base portion 520 or is attached to the shaft fixed to the head support portion 580 when the head support portion 580 is fixed to the base portion 520 and is rotatable about the shaft.

Figure 9A:
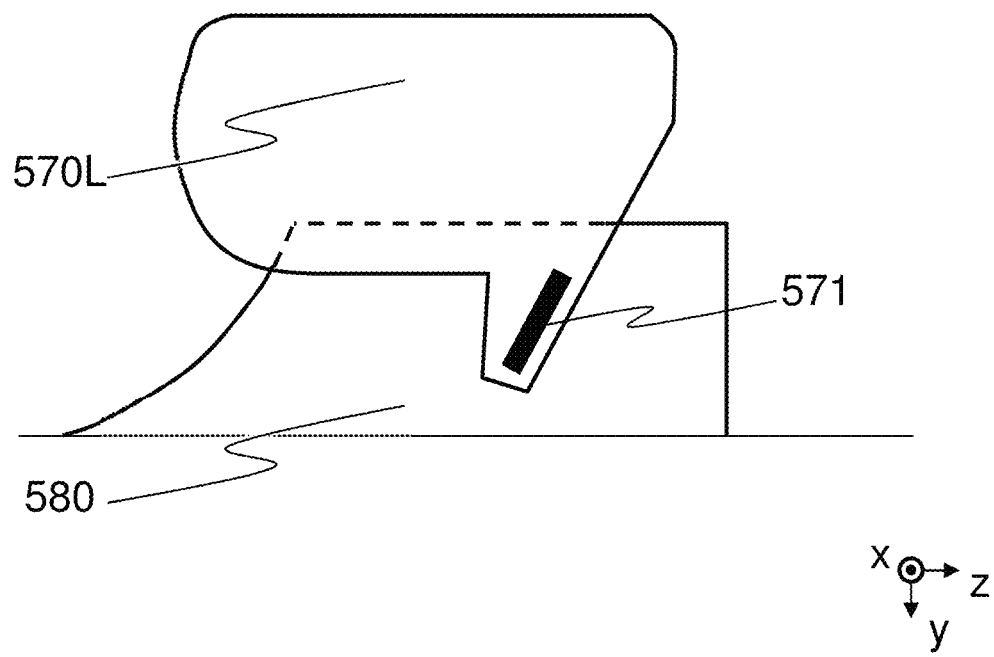
FIGS. 9A and 9B are schematic diagrams describing a support mechanism of a side coil, where
Figure 9B:
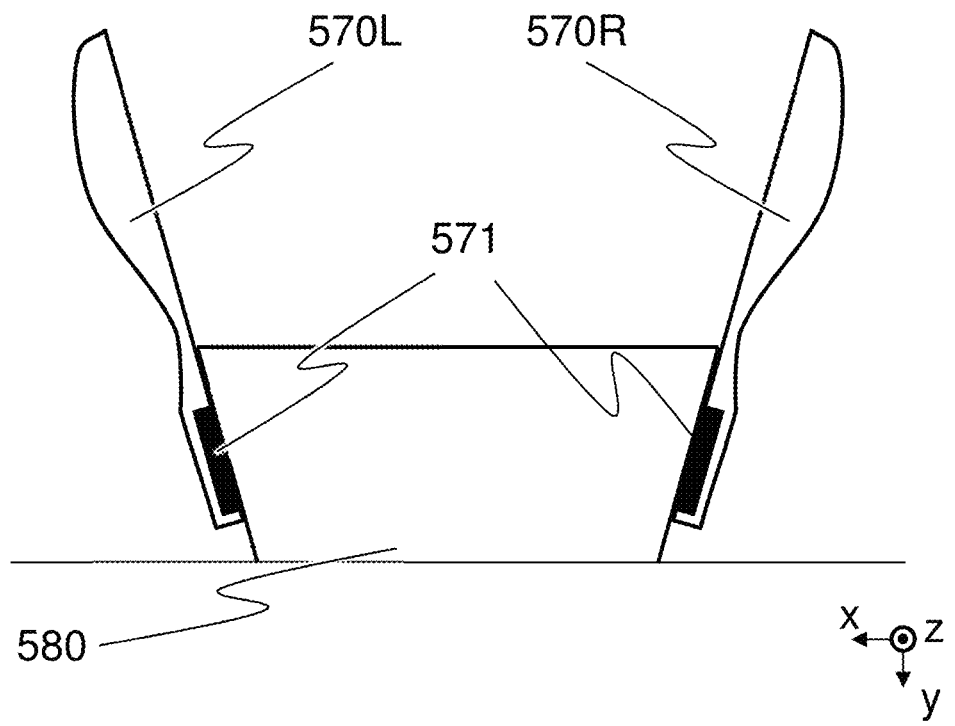

As an example, an embodiment in which the side panel 570 is fixed to the head support portion 580 is illustrated in FIGS. 9A and 9B.

Figure 10:
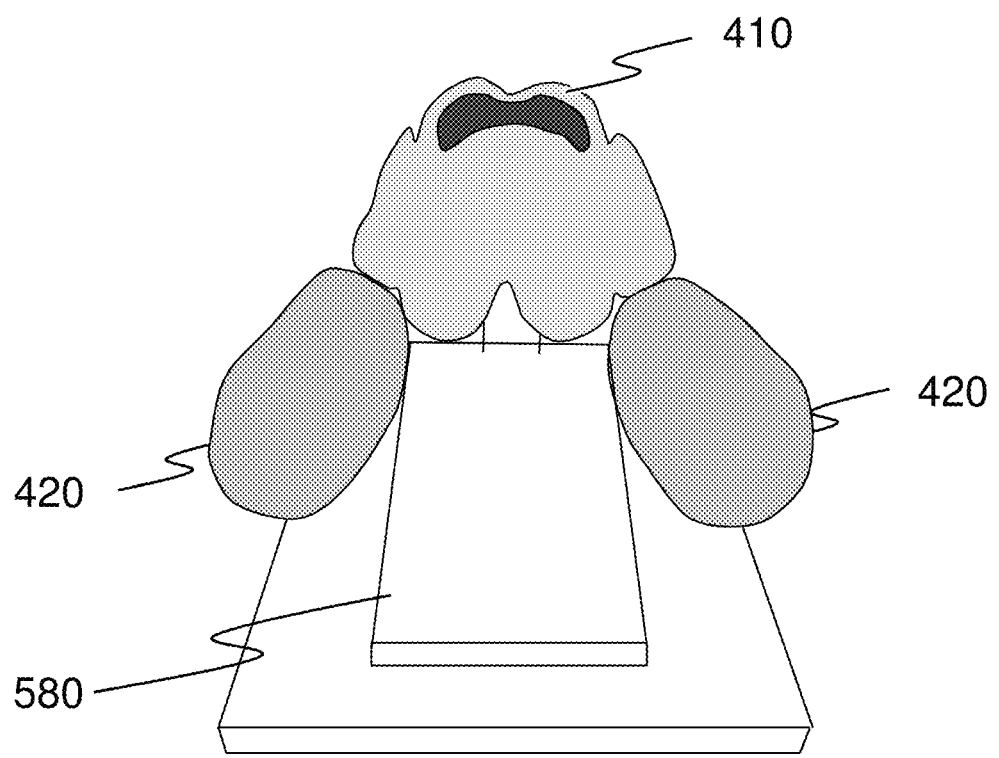
FIG. 10 is a front view illustrating a state in which the side coil is opened (a retracted state of the coil device)

An attachment shaft 571 of the side panel 570 is not perpendicular to the upper surface of the base portion 520 and is inclined with respect to the Z direction and the X direction. That is, the attachment shaft is inclined backward in the Z direction as illustrated in FIG. 9A and the attachment shaft is inclined in the X direction so that the right and left side panels 570L and 570R are opened in the X direction as illustrated in FIG. 9B. Accordingly, when the side panel 570 located at the position of FIG. 9A is rotated about the shaft 571, the side panels 570 are opened toward both sides and are retracted backward. That is, in a state before a coil device is attached to the subject, the side coils 420 are retracted right and left so that a large space is open as illustrated in FIG. 10. When the subject is placed on the head support portion 580 in this state and the side panels 570 are rotated, the side panels 570 are positioned and attached to both sides of the subject from the rear and side positions as illustrated in FIG. 9B.

The coil device of this embodiment realizes the rotation of the side panel 570 about the attachment shaft 571 by the movement of the holder 540 (interlocking opening/closing function). A configuration for this will be described with reference to FIGS. 11A and 11B.

Figure 11A:
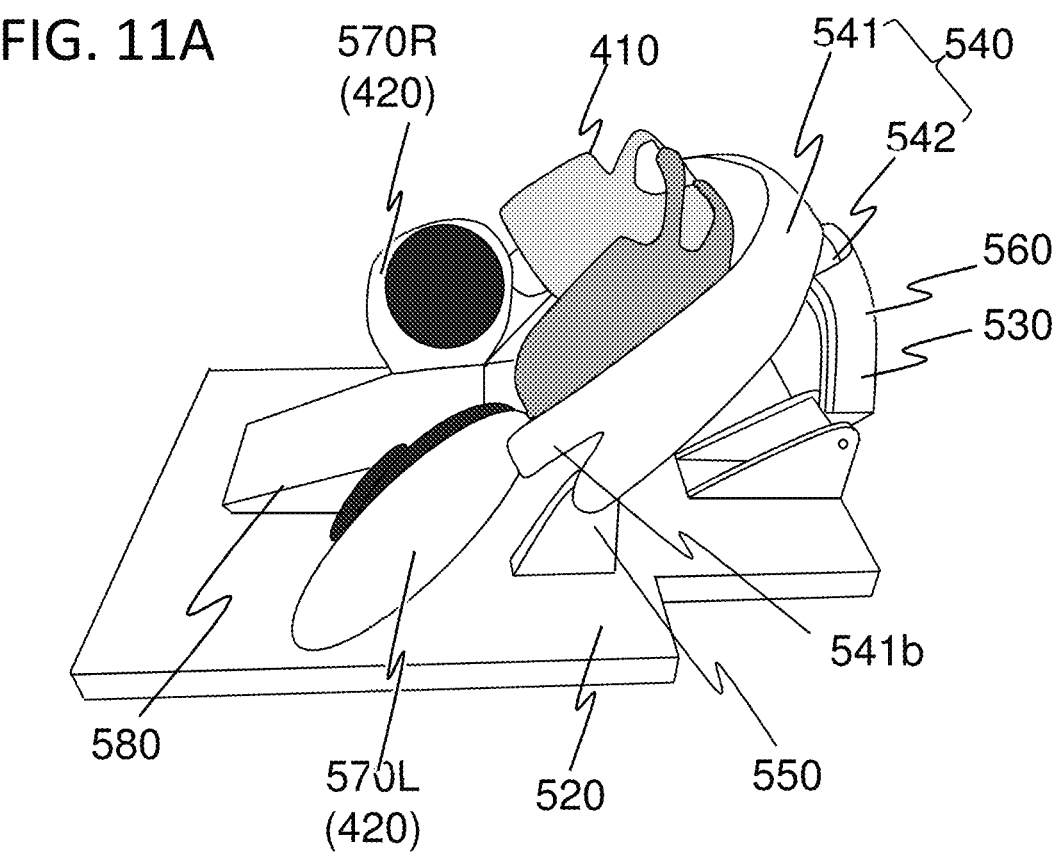
FIGS. 11A and 11B are diagrams describing a relationship between a movement of a holder and a movement of a side panel, where
Figure 11B:
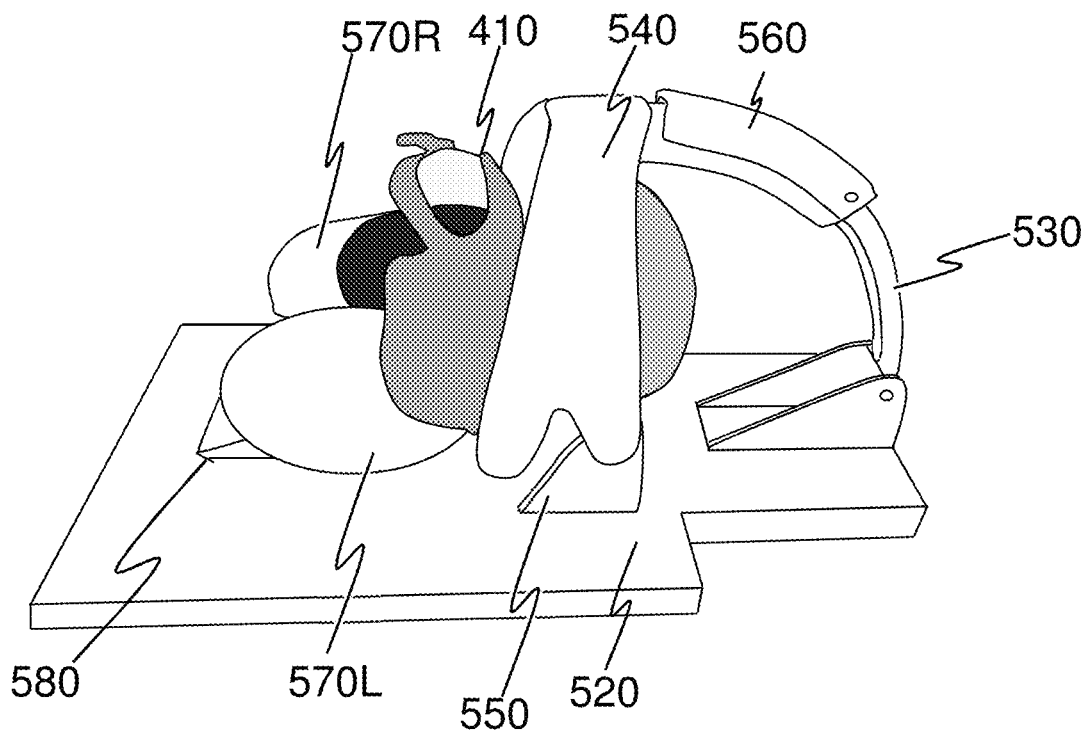

As illustrated in FIG. 11A, when the holder 540 is in the retracted state, the side panel 570 is also located at the retracted position and the front end 541*b* of the first holder portion 541 is located at the outside of the side panel 570. When the holder 540 is moved from this state to the attached position with respect to the support body 530, the front end 541*b* also moves toward the center side while pressing the rear surface of the side panel 570. The side panel 570 rotates about the attachment shaft 571 (FIGS. 9A and 9B) due to the movement of the front end 541*b*, the portion of the side panel 570 first coming into contact with the front end 541*b* enters the face coil 410, and the face coil 410 and the side coil 420 are finally attached to the head of the subject while being integrated with each other as illustrated in FIG. 11B. In this way, the face coil 410 and the side coil 420 can be attached to the subject just by the operation of the holder 540 for attaching the face coil 410 to the subject (the operation of the holder through the handle 560).

Further, although the rear coil 430 is not illustrated in FIGS. 11A and 11B, the rear coil 430 is continuously disposed inside the housing of the coil device from the head support portion 580 to the base portion 520. In this way, even when the rear coil 430 is added, three coil units 410 to 430 can be attached to the subject by the same operation.

Further, when the holder 540 is operated to move to the retracted position (FIG. 11A), the side panel 570 rotates about the attachment shaft 571 to be opened (FIG. 10) by the weight of the fixed side coil 420 and the weight of the side panel and moves to the outer retracted position.

In this way, the coil device of this embodiment can attach the head coil including the side coil 420 to the subject or detach the head coil therefrom just by operating the handle 560 provided in the holder 540 while the head of the subject is placed on the base portion 520.

Further, a case in which the side coil 420 is disposed at both sides is illustrated in the drawing, but the side coil may be provided only at one side in some cases. For example, in FIGS. 11A and 11B, a case in which the subject is disposed in the head coil device so that the face faces up (in the supine position) is illustrated, but the subject may be disposed so that the face faces the side. In that case, the plate surface of the base portion 520 is disposed vertically and only one upper coil is used as the side coil.

[Fixing Belt]

Next, a fixing belt for improving the close contact state between the coil unit (the face coil) and the subject after the attachment operation will be described.

Figure 12:
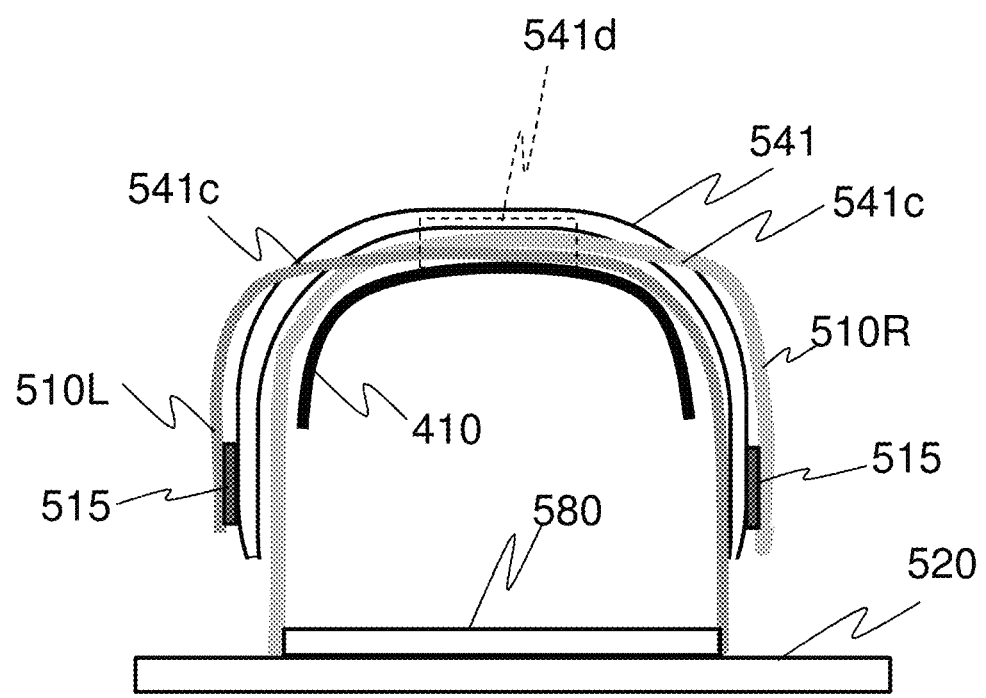
FIG. 12 is a diagram illustrating an example of a fixing belt.

In this embodiment, one end of the fixing belt is detachably fixed to the head support portion 580 or the base portion 520 through the rotation shaft. Accordingly, the fixing belt can be replaced (changeable) by pulling the fixing belt up from the rotation shaft during the maintenance. Further, a surface fastener is adhered to the other end (free end) and the other end is fixed to the holder 540 by the surface fastener. Specifically, as illustrated in FIG. 12, one of a pair of surface fasteners 515 is adhered to both ends of the first holder portion 541 (the vicinity of the bifurcated part), the other end of the surface fastener is adhered to each end of two fixing belts 510R and 510L (510 when both of them are not distinguished), and the holder 540 and the fixing belt 510 are fixed to each other by the adhering between the surface fasteners 515.

Holes (slit-like holes) 541*c* through which the fixing belt 510 passes are formed at both sides of the first holder portion 541 with the center portion interposed therebetween. The left fixing belt 510L passes through the right hole 541*c* inside the housing of the coil device to be exposed to the outside of the first holder portion 541 and passes through the outside of the side panel 570 so that the end of the fixing belt is fixed to the surface fastener 515 attached to the right front end. Similarly, the right fixing belt 510R passes through the left hole 541*c*, passes through the outside of the left side panel 570, and is fixed to the left front end. By adjusting the fixing position of the surface fastener, the coil unit 400 can be in close contact with the subjects of various subject sizes. In this way, when the surface fastener is used to fix the fixing belt 510, the fixing belt can be easily attached or detached for replacement and operability is improved, in contrast to that fixing with screws or dials takes time to release in an emergency such as vomiting of the subject.

Furthermore, the size (width) of the hole 541*c* is set to be smaller than the thickness of the front end to which the surface fastener of the fixing belt 510 is fixed. Accordingly, the fixing belt 510 is prevented from falling out of the hole 541*c*. Further, the first holder portion 541 may be provided with a fall preventing wall (dotted line: 541*d*) which prevents the fixing belt 510, protruding from the hole 541*c* to the outside of the holder, from slipping off. The fall preventing wall 541*d* can be provided as, for example, a separate component from or integrated with the holder body in the vertical direction with respect to the plane direction of the holder on the front side of the center portion of the first holder portion 541 (on the side opposite to the portion connected to the second holder portion 542).

With the above-described configuration, the fixing belt 510 is fastened with high operability and the close contact state of the coil unit with respect to the subject can be improved. As a result, the signal reception sensitivity can be increased and the image quality of the MR image can be improved.

Additionally, in this embodiment, an example in which the surface fastener 515 is adhered to both right and left sides of the first holder portion 541 in order to fix the fixing belt 510 to the holder 540 is illustrated, but the invention is not limited thereto. For example, two fixing belts may be fastened to either right or left side. Accordingly, an access to the opposite side where the technician is standing can be reduced.

Further, for example, the fixing belt 510 may be one and may be fastened to the surface fastener adhered to either right or left so that the fixing belt 510 passes through both right and left sides. In this case, an access to the opposite side where the technician is standing can be reduced and the fixing belt 510 can be operated with one hand.

[Coil Attaching Operation]

Next, an operation of attaching the coil unit 400 to a subject using the coil device of this embodiment will be described with reference to FIGS. 11A and 11B. FIG. 11A is an explanatory diagram illustrating a retracted state of the coil device and FIG. 11B is an explanatory diagram illustrating an attached state. Here, the subject is not illustrated in order to easily show the structure.

First, in the standby state illustrated in FIG. 11A, the subject is laid down on the head support portion 580 in the supine position. In this state, as illustrated in FIG. 10, since the side panels 570 are wide open to the right and left, there is no rigid structure that interferes with the supporting hand even when the subject is laid down while supporting the rear side of the head of the subject. Accordingly, it is easy to lay down the subject. The state of FIG. 11A can be changed to the state of FIG. 11B in such a manner that the coil operator just holds and slides the unlocking handle 560 with a hand. At this time, since the front end 541b of the holder 540 presses the side panel 570, the side panel 570 and the side coil 420 fixed thereto can also move to the vicinity of the subject in an interlocking manner. Then, two right and left fixing belts 510 (FIG. 12) are pulled and the fixing belt 510 is fixed to the holder 540 by a surface fastener or the like. As described above, the installing and fixing operation of the coil unit 400 of this embodiment with respect to the subject is completed.

Accordingly, the time required for the conventional work to fill and fix the sponge can be shortened. Further, a fixing operation is generally performed in a narrow space between the coil housing and the subject, but in this embodiment, since the fixing belt 510 can be operated by using a wide space outside the coil unit 400, the physical burden due to the technician's posture can be reduced. Further, since the fixing belt 510 passes through the hole 541c in the upper portion of the holder 540, the fixing belt 510 on the opposite side of the bed is also easily reached. Accordingly, the technician working in either right or left side of the bed can also easily operate the fixing belt. Further, since the fall preventing wall 541d of the fixing belt 510 is provided between the face coil 410 and the holder 540, there is no risk that the fixing belt 510 falls onto the eye of the subject.

In the coil device of this embodiment, an operation of preventing deterioration of image quality by preventing magnetic coupling between the sub-coils when the face coil 410 and the side coil 420 (further, the rear coil 430) are disposed in close contact with the subject 103 will be described again with reference to the circuit diagram of FIG. 5B.

When the angular frequency with respect to the nuclear magnetic resonance frequency is ω, the capacitance of the parallel capacitor 324 is $C_m$, and the input impedance of the low impedance signal processing circuit 351 is $Z_{in}$, the block impedance is represented by the following equation (1).

(Math. 1)

$$Z_{block} = 1/\omega^2 C_m^2 Z_{in})  \quad (1)$$

Since $C_m$ becomes smaller as the distance between the loop coil unit 320 and the subject 103 becomes smaller, it is possible to improve the block impedance by the configuration capable of realizing the close arrangement. Accordingly, it is possible to improve the function of preventing magnetic coupling between the sub-coils and to prevent deterioration of image quality.

Modified Example of First Embodiment

In the coil device of the first embodiment, some elements can be added in addition to the above-described configuration or a part of the members constituting the coil device can be configured as another member having the same function. Hereinafter, modified examples of this embodiment will be described.

Modified Example 1: Mirror

An example of an additional element is a mirror that allows the subject to see the outside of the device. The subject to which the coil device is attached is inserted into a narrow static magnetic field space of the MRI apparatus (FIGS. 1A and 1B) so that a visual field is limited. In this modified example, the mirror is attached to the coil device to have a predetermined angle so that the subject can see the outside.

Figure 13A:
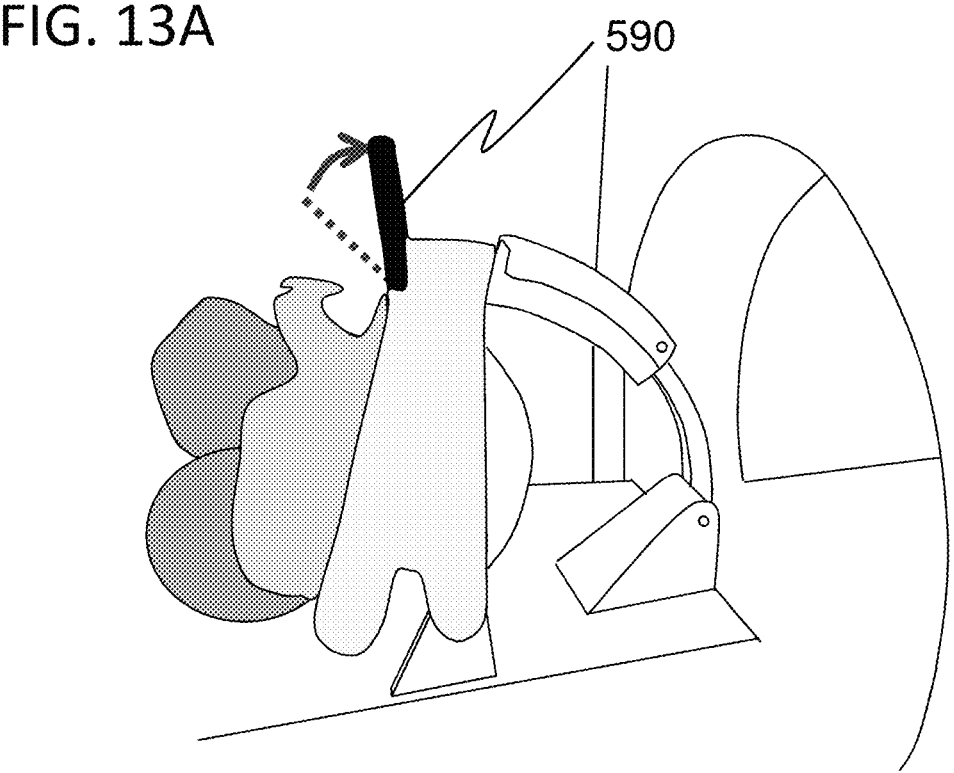
FIGS. 13A and 13B are diagrams illustrating an embodiment of a holder to which a mirror is attached, where
Figure 13B:
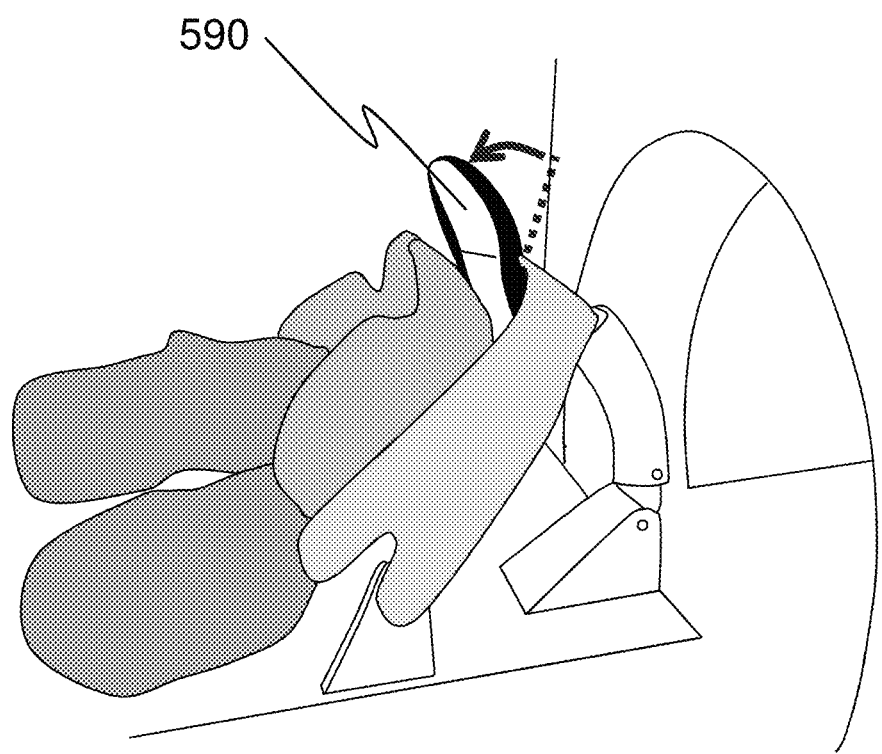

An attachment example of the mirror and a structure for setting an appropriate angle will be described with reference to FIGS. 13A and 13B. As illustrated in FIG. 13A, a mirror 590 is attached in front of the first holder portion 541 so that the mirror surface faces the outside. For example, the mirror 590 is attached to the block member 545 (FIG. 7B) for fixing the face coil 410 in the first holder portion 541 through the attachment shaft in the X direction so as to be rotatable. Accordingly, as illustrated in FIG. 13B, the mirror 590 can change an angle with respect to the first holder portion 541. In a state in which no external force is applied to the mirror 590, the mirror is urged so that an angle with respect to the front surface of the first holder portion illustrated in FIG. 13A is small.

Figure 14A:
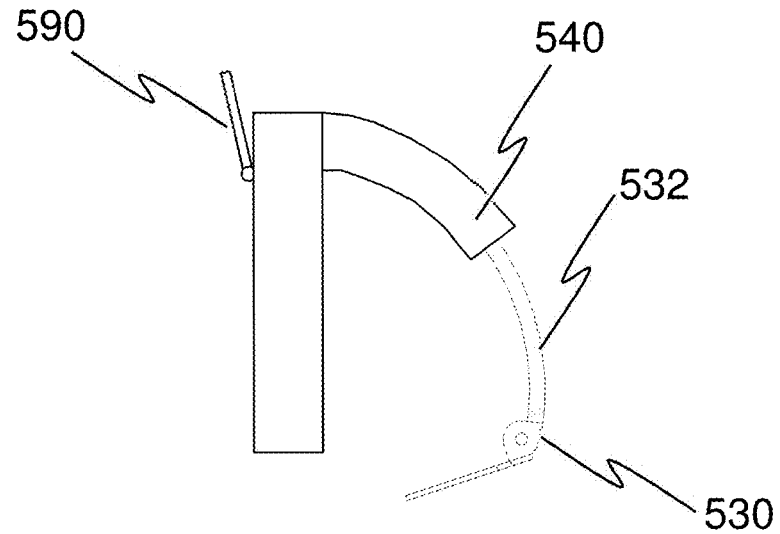
FIGS. 14A to 14C are diagrams describing a relationship between a movement of a mirror and a front end shape of a support body (curved portion), where
Figure 14B:
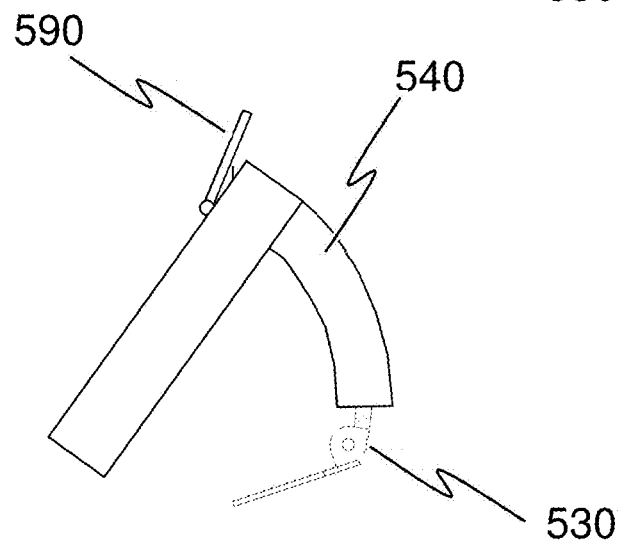
Figure 14C:
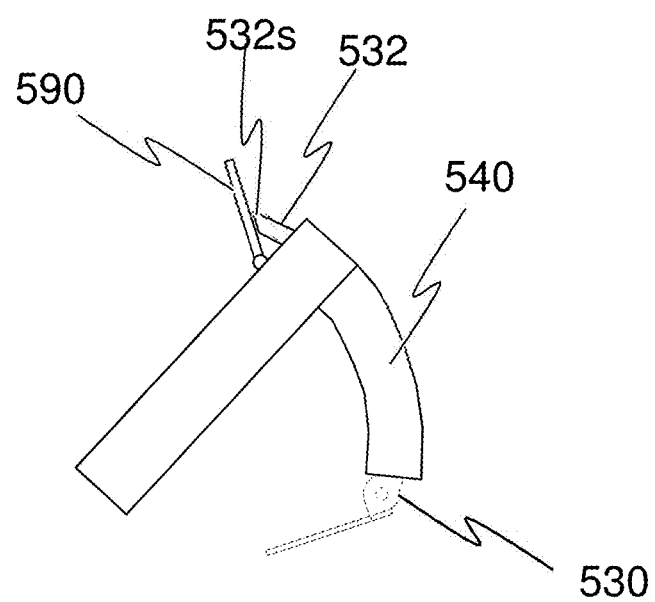

Specifically, as illustrated in FIG. 14A, the mirror 590 has a substantially perpendicular angle at a position of the holder 540 where the face coil is attached to the subject. On the other hand, when the holder 540 is slid to the retracted state, the second holder portion 542 moves along the curved portion 532 of the support body 530 (FIG. 14B) and the front end of the curved portion 532 protrudes from the cylindrical portion of the second holder portion 542 to reach the rear surface of the mirror 590 (FIG. 14C). As illustrated in FIG. 8A, the front end of the curved portion 532 is provided with an inclined surface 532s and the inclined surface 532s presses the mirror surface so that the mirror 590 rotates about the attachment shaft to have an angle parallel to the inclined surface 532s. The angle of the inclined surface 532s is, for example, about 45° with respect to the surface orthogonal to the shaft of the curved portion 532. Accordingly, in the retracted state illustrated in FIG. 14C, the mirror surface of the mirror 590 opens at an angle with respect to the first holder portion 541 so that the subject can see the view on the foot side, that is, the outside of the MRI apparatus.

Figure 15:
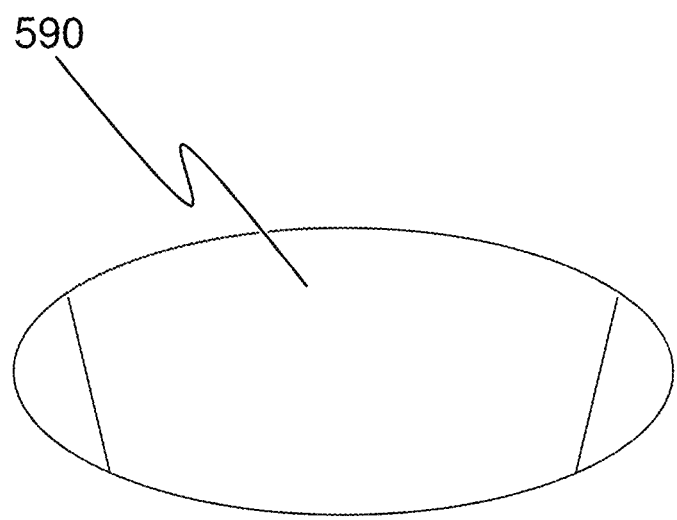
FIG. 15 is a diagram describing a shape of a mirror surface of a mirror.

Here, since the mirror surface of the mirror 590 is formed into a trapezoidal shape that opens from the bottom to the top as illustrated in FIG. 15, the view reflected on the mirror becomes a view cut out in a rectangular shape and the outside can be viewed without a sense of discomfort.

Modified Example 1: Handle

As another example of an additional element, the coil device of this embodiment may have an additional handle. For example, the handle can be provided in a space between the face coil 410 and the support body 530 with respect to the base portion 520. Accordingly, the space required on the parietal side can be minimized. Further, a handle can be added by forming a hole in the upper surface of the base portion 520 on the neck side. Accordingly, the handle can be gripped even when the spine coil is continuously installed at the neck end. Since these two handles are disposed with the center of gravity of the coil unit 400 interposed therebetween, it is easy to maintain a balance when carrying the subject. Further, since it is not necessary to reach the right and left sides, even a short technician can easily access the handle. From the above, operability when carrying the subject is improved.

Modified Example 3: Support Body

Figure 16A:
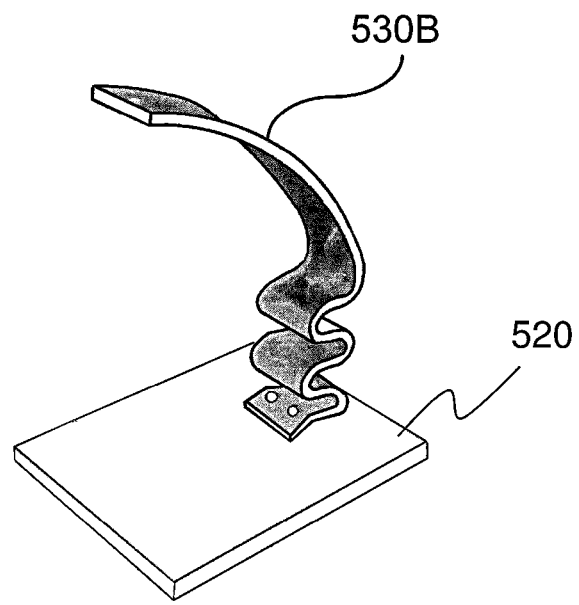
FIGS. 16A and 16B are diagrams respectively illustrating modified examples of support bodies.
Figure 16B:
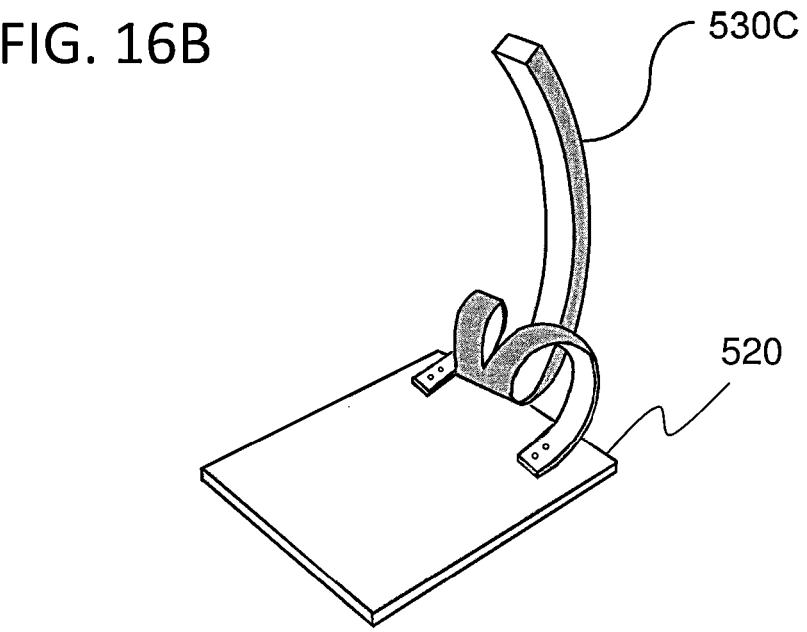

In the first embodiment, a configuration is illustrated in which the support body 530 includes a hinge shaft, that is, the curved portion 532 is connected to the fixed portion 531 having a leaf spring by a hinge shaft, but the structure of the support body 530 is not limited thereto. For example, the hinge shaft portion may be removed. An example of the support body in this case is illustrated in FIGS. 16A and 16B. FIG. 16A illustrates a support body 530B having a wavy shape below the curved portion 532 and FIG. 16B illustrates a support body 530C in which the lower side of the curved portion 532 (the side fixed to the base portion 520) is divided into right and left parts and each has a spiral shape in a direction parallel to the base surface of the base portion 520. In any of the examples, the whole can be manufactured by integral molding.

According to these structures, it is possible to ensure the movement range of the coil unit 400 and the holder 540 fixed to the support body 530 in the up and down direction and the vertical direction similarly to the structure of the first embodiment. That is, it is possible to perform the coil device attaching operation in which the holder 540 is slid in a curved shape and is pressed against the head of the subject in a close contact state.

Further, since the support bodies 530B and 530C of these modified examples have a structure simpler than a structure having a hinge shaft, the number of components can be reduced and members can be easily manufactured.

Second Embodiment

The first embodiment is an embodiment in which the coil device is used as the RF receiving coil of the MRI apparatus, but in this embodiment, an array coil (coil unit) including a plurality of sub-coils is used as the RF transmitting coil 151 instead of the birdcage type RF coil 300 shown in FIG. 3. In the coil device of this embodiment, the configuration of the coil support portion excluding the coil unit is the same as that of the first embodiment and redundant description is omitted.

Figure 17A:
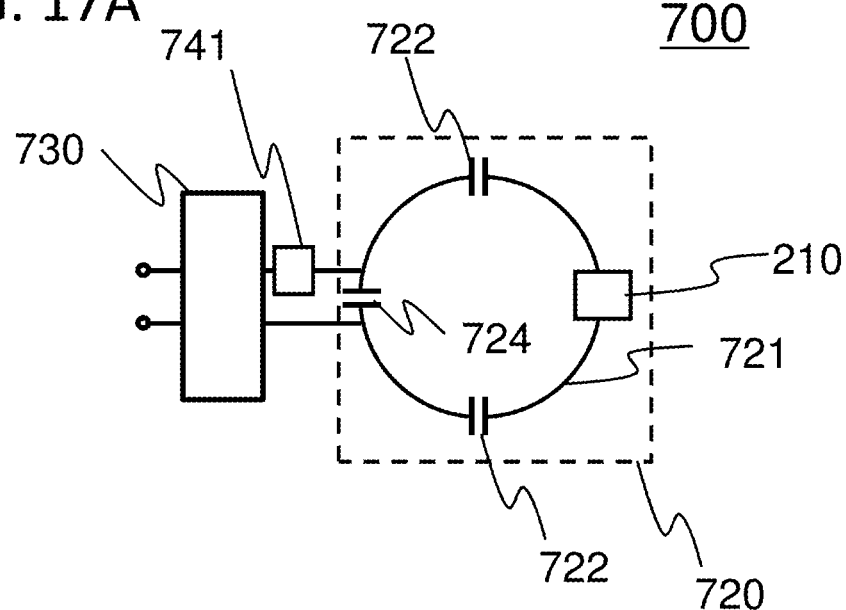
FIGS. 17A and 17B are circuit diagrams of a coil unit of a coil device (RF transmitting coil) of a second embodiment, where

The array coil used as the RF transmitting coil 151 also includes one or more sub-coils as illustrated in FIG. 5A, but the circuit portion of each sub-coil is different. FIG. 17A illustrates a circuit portion of one sub-coil 700 constituting an array coil.

Each sub-coil 700 basically has the same configuration as that of the sub-coil 300 (FIG. 5B) of the first embodiment. However, a loop coil unit 720 is not connected to the low input impedance signal processing circuit 351, but is connected to a low output impedance signal processing circuit 730 via a magnetic coupling adjusting unit 741. A low output impedance RF amplifier (a low output impedance signal amplifier) can be used as the low (output) impedance signal processing circuit 730.

Further, a transmitting array coil includes the transmission/reception magnetic coupling prevention circuit 210 as a transmission/reception magnetic coupling prevention circuit that prevents magnetic coupling between the transmitting RF coil and the receiving RF coil.

Figure 17B:
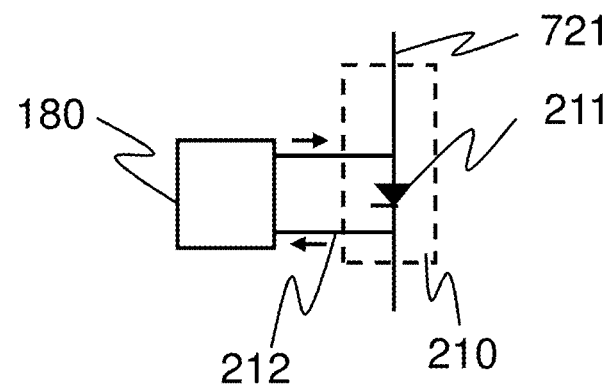

FIG. 17B is a diagram for describing the configuration and the connection of the transmission/reception magnetic coupling prevention circuit 210. The transmission/reception magnetic coupling prevention circuit 210 includes a PIN diode 211 and a control signal line 212. The PIN diode 211 is inserted in series into a straight conductor (loop) 721 and the control signal line 212 is connected to both ends of the PIN diode 211. The control signal line 212 is connected to the magnetic coupling prevention circuit driving device 180. A choke coil is inserted into the control signal line 212 in order to prevent the mixing of high frequencies.

The PIN diode 211 normally exhibits a high resistance (OFF) and becomes substantially conductive (ON) when the value of the direct current flowing in the forward direction of the PIN diode 211 becomes a certain value or more. In this embodiment, the ON/OFF state of the PIN diode 211 is controlled by the direct current output from the magnetic coupling prevention circuit driving device 180 by using this characteristic. That is, when transmitting the high-frequency signal, a control current flows so that the PIN diode 211 becomes a conductive state and the array coil (sub-coil 700) functions as the RF transmitting coil 151. Further, when receiving the nuclear magnetic resonance signal, the flow of the control current is stopped so that the array coil (sub-coil 700) has high impedance to be an open state.

In this way, in this embodiment, the array coil functions as the RF transmitting coil 151 when transmitting the high-frequency signal and magnetic coupling with the array coil corresponding to the RF receiving coil 161 is removed in an open state when receiving the nuclear magnetic resonance signal by controlling the direct current (the control current) from the magnetic coupling prevention circuit driving device 180.

The adjustment of each circuit element is basically the same as that of the array coil of the first embodiment and is performed by a series capacitor 722 inserted in series into a loop 721 of the loop coil unit 720, a parallel capacitor 724 inserted in parallel, and the magnetic coupling adjusting unit 741.

When transmitting a signal, a low output impedance signal amplifier 731 seen from each of the sub-coils 700 constituting the transmitting array coil has low impedance. Accordingly, each sub-coil 700 of the transmitting array coil forms the same current distribution as each sub-coil 300 of the receiving array coil 400A of the first embodiment and resonates, for example, at a nuclear magnetic resonance frequency of 64 MHz of hydrogen at a static magnetic field strength of 1.5 T (tesla).

As described above, since each sub-coil 700 constituting the transmitting array coil of this embodiment resonates at a desired frequency (for example, 64 MHz), RF can be transmitted with high efficiency. At the same time, since the coil device can be disposed in a close contact state according to various head shapes, the sensitivity is improved similarly to the first embodiment. Therefore, the transmission efficiency is improved and the power required for imaging can be reduced.

Further, the plurality of sub-coils 700 are not coupled to each other and have sensitivity regions different from those of other sub-coils. Therefore, the sub-coils function as a multi-channel.

Additionally, this embodiment can be also applied to all of the MRI apparatus 100 including the horizontal magnetic field type magnet 110 and the MRI apparatus 101 including the vertical magnetic field type magnet 111 similarly to the first embodiment.

As described above, according to each embodiment, since the coil device can be attached to the subject in a close contact state regardless of the size of the head of the subject without deteriorating the operability or durability, a high-quality MRI image can be provided.

What is claimed is:

1. A head coil device comprising:
a first coil unit, which has a first coil element and covers a front head of the head;
a second coil unit, which has a second coil element and covers at least one side surface of the head;
a base portion;
a support body which is connected to the base portion and has an elastic member; and
a holder which connects the support body to the first coil; and
two guide portions respectively disposed on sides of the base portion and fixed to the base portion and that each contact the holder,
wherein the holder is supported at three contact points including the two guide portions and support body, and
wherein the holder is elastically in contact with the respective two guide portions.

2. The head coil device according to claim 1,
wherein the holder is slidably supported on the support body at one center position.

3. The head coil device according to claim 1,
wherein the holder includes a first holder portion which is curved along a shape of the first coil unit and a second holder portion which is curved in a direction intersecting the first holder portion, and
wherein the support body includes a curved portion which slidably supports the second holder portion in a curved shape.

4. The head coil device according to claim 3, further comprising:
a lock mechanism portion which is provided between the second holder portion and the curved portion to lock and unlock the sliding of the second holder portion with respect to the curved portion.

5. The head coil device according to claim 1,
wherein the base portion includes a head support portion on which the head of the subject is placed and a side panel portion which fixes the second coil unit, and
wherein the side panel portion is fixed to the head support portion through a support shaft and is rotatable about the support shaft.

6. The head coil device according to claim 5,
wherein the side panel portion is opened and closed while being interlocked with the sliding of the holder.

7. The head coil device according to claim 5,
wherein when the right and left direction of the head is an X direction and the up and down direction of the head is a Z direction, the support shaft has an inclination in at least one of the X direction and the Z direction with respect to an upper surface of the base portion and urges the side panel portion in a direction moving away from the head.

8. The head coil device according to claim 6,
wherein the holder is located at a position in which a front end contacts the side panel portion, the front end moves in accordance with the sliding of the holder, and the side panel portion is rotated in a direction in which the side panel portion is in close contact with the head.

9. The head coil device according to claim 1,
wherein the first coil unit and a side panel portion including the second coil unit are partially flexible.

10. The head coil device according to claim 1,
further including a third coil unit which covers a rear portion of the subject.

11. The head coil device according to claim 1, further comprising:
a fixing belt which allows the first coil unit to be in close contact with the head of the subject,
wherein one end of the fixing belt is fixed to the base portion and the holder is provided with a notch or hole for passing the fixing belt therethrough.

12. The head coil device according to claim 1,
wherein when the support side of the holder with respect to the support body is a rear side and the opposite side thereof is a front side, a mirror having a mirror surface formed in front side is rotatably attached to the holder.

13. The head coil device according to claim 12,
wherein the support body is formed such that an end surface of an end opposite to an end fixed to the base portion has a predetermined angle with respect to an axial direction of the support body, the end surface of the end comes into contact with the mirror at a lower limit position of a slidable range of the holder, and an angle of the mirror with respect to the holder is defined.

14. The head coil device according to claim 1,
wherein the first coil unit includes a coil loop portion which is formed of a conductor and a cover member that covers the coil loop portion and the cover member is provided with a transmissive portion for ensuring a visual field of the subject when the first coil unit is attached to the subject in an area in which the conductor of the coil loop portion does not exist.

15. The head coil device according to claim 1,
wherein the support body includes a fixed portion which is fixed to the base portion and a curved portion which is formed to be continuous to the fixed portion and has a curved shape and the fixed portion has a structure with mechanical elasticity.

16. The head coil device according to claim 15,
wherein the fixed portion has a leaf spring or has a corrugated shape or spiral shape in cross-section.

17. The head coil device according to claim 1,
wherein the first coil unit includes an array coil in which a plurality of sub-coils are arranged and an adjusting element which prevents magnetic coupling between the sub-coils, and a distance between the sub-coils is variable.

18. A magnetic resonance imaging apparatus comprising:
a transmitting coil which applies a high-frequency magnetic field to a subject;
a receiving coil which detects a nuclear magnetic resonance signal generated from the subject; and
a signal processing unit which reconstructs an image of the subject by using the nuclear magnetic resonance signal, wherein the coil device according to claim 1 is used as the receiving coil.

19. A magnetic resonance imaging apparatus comprising:
a transmitting coil which applies a high-frequency magnetic field to a subject;
a receiving coil which detects a nuclear magnetic resonance signal generated from the subject; and
a signal processing unit which reconstructs an image of the subject by using the nuclear magnetic resonance signal,
wherein the coil device according to claim 1 is used as the transmitting coil.

* * * * *